US012657642B2

(12) United States Patent
Senda

(10) Patent No.: US 12,657,642 B2
(45) Date of Patent: Jun. 16, 2026

(54) INFORMATION MONITORING DEVICE, INFORMATION MANAGEMENT SYSTEM, IMMIGRATION INSPECTION METHOD, ADMISSION MANAGEMENT METHOD, AND COMPUTER-READABLE RECORDING MEDIUM STORING INFORMATION MANAGEMENT PROGRAM

(71) Applicant: SUN WISE Co., Ltd., Osaka (JP)

(72) Inventor: Yasushi Senda, Kobe (JP)

(73) Assignee: SUN WISE CO., LTD., Osaka (JP)

( * ) Notice: Subject to any disclaimer, the term of this patent is extended or adjusted under 35 U.S.C. 154(b) by 504 days.

(21) Appl. No.: 18/145,029

(22) Filed: Dec. 22, 2022

(65) Prior Publication Data

US 2023/0130214 A1 Apr. 27, 2023

Related U.S. Application Data

(63) Continuation-in-part of application No. PCT/JP2021/020966, filed on Jun. 2, 2021.

(30) Foreign Application Priority Data

Jun. 26, 2020 (JP) ................................. 2020-110146

(51) Int. Cl.
G06Q 50/26 (2012.01)
A61B 5/00 (2006.01)
A61B 5/01 (2006.01)

(52) U.S. Cl.
CPC ............. G06Q 50/265 (2013.01); A61B 5/01 (2013.01); A61B 5/68335 (2017.08);
(Continued)

(58) Field of Classification Search
CPC .... G06Q 50/265; G06Q 10/02; G06Q 30/018; G06Q 50/26; A61B 5/01; A61B 5/68335;
(Continued)

(56) References Cited

U.S. PATENT DOCUMENTS 4,294,263 A 10/1981 Hochman
2002/0115921 A1* 8/2002 Berlin .................. G01N 33/528
600/362

(Continued)

FOREIGN PATENT DOCUMENTS

JP S56-052036 A 5/1981
JP S61-226783 A 10/1986
(Continued)

OTHER PUBLICATIONS

Extended European Search Report (EESR) dated Oct. 26, 2023 in EP Patent App No. 21828413, which is EP counterpart of present application. Submitted additionally for all other references listed on this IDS.

(Continued)

*Primary Examiner* — Omar Casillashernandez
(74) *Attorney, Agent, or Firm* — Kratz, Quintos & Hanson, LLP

(57) ABSTRACT

An information monitoring device for monitoring information includes a temperature sensor that detects a body temperature from a person, a detection controller that performs control on the temperature sensor so that the temperature sensor repeats detection of the body temperature, a holding member that attaches the temperature sensor to the person to hold the temperature sensor, and an optical sensor that detects removal of the temperature sensor from the person.

21 Claims, 14 Drawing Sheets

(52) U.S. Cl.
CPC .... *A61B 5/6844* (2013.01); *A61B 2562/0271*
(2013.01); *A61B 2562/185* (2013.01)

(58) Field of Classification Search
CPC .......... A61B 5/6844; A61B 2562/0271; A61B
2562/185; A61B 2560/0266; A61B
2562/0233; A61B 5/0008; A61B 5/6843;
A61B 2560/0209; A61B 2562/08; A61B
5/0022; A61B 5/6813
USPC ........................................................ 340/502
See application file for complete search history.

(56) References Cited

U.S. PATENT DOCUMENTS

| | | | | |
|---|---|---|---|---|
| 2006/0178567 | A1 * | 8/2006 | Goh | G01S 5/0018 |
| | | | | 128/920 |
| 2009/0234200 | A1 | 9/2009 | Husheer | |
| 2015/0028996 | A1 | 1/2015 | Agrafioti et al. | |
| 2018/0070841 | A1 * | 3/2018 | Honore | A61B 5/02007 |
| 2019/0329056 | A1 | 10/2019 | Sjoquist et al. | |
| 2023/0274117 | A1 * | 8/2023 | O'Bryan | G06K 7/0008 |
| | | | | 340/572.1 |

FOREIGN PATENT DOCUMENTS

| | | | | | |
|---|---|---|---|---|---|
| JP | 2000-123098 | A | | 4/2000 | |
| JP | 2009-535141 | A | | 10/2009 | |
| JP | 2020-024133 | A | | 2/2020 | |
| WO | 2015-051253 | A3 | | 4/2015 | |
| WO | WO-2015051253 | A2 | * | 4/2015 | .......... A61B 5/0452 |
| WO | WO-2015081321 | A1 | * | 6/2015 | .......... A61B 5/0022 |
| WO | WO-2015100109 | A1 | * | 7/2015 | .......... A61B 5/0004 |
| WO | 2017/105600 | A1 | | 6/2017 | |
| WO | WO-2017182456 | A1 | * | 10/2017 | ........ A61B 5/02416 |
| WO | WO-2017214772 | A1 | * | 12/2017 | .......... A61B 5/0008 |
| WO | 2018-049412 | A8 | | 3/2018 | |
| WO | WO-2018049412 | A1 | * | 3/2018 | .......... A61B 5/0022 |
| WO | WO-2019161858 | A1 | * | 8/2019 | .......... A61B 5/0002 |

OTHER PUBLICATIONS

Communication pursuant to Article 94(3) EPC for European Patent
Application No. 21828413.1 issued Apr. 25, 2025 (8 sheets).

* cited by examiner

| Nationality | Gender | Age | Height (cm) | Blood type | Normal body temperature (°C) | Variation range (±) |
|---|---|---|---|---|---|---|
| Japan | Male | 0 | 40 | A | 36.5 | 0.5 |
| · | · | · | · | · | · | · |
| Japan | Male | 10 | 140 | B | 36.6 | 0.2 |
| · | · | · | · | · | · | · |
| Japan | Male | 15 | 160 | AB | 36.7 | 0.3 |
| · | · | · | · | · | · | · |
| Japan | Male | 20 | 170 | O | 36.5 | 0.4 |
| · | · | · | · | · | · | · |
| Japan | Male | 75 | 160 | B | 35.8 | 0.8 |
| · | · | · | · | · | · | · |
| Japan | Female | 12 | 140 | A | 36.6 | 0.2 |
| · | · | · | · | · | · | · |
| Japan | Female | 25 | 160 | O | 36.0 | 0.4 |
| · | · | · | · | · | · | · |
| USA | Male | 15 | 170 | AB | 36.7 | 0.3 |
| · | · | · | · | · | · | · |
| USA | Female | 30 | 175 | O | 36.0 | 0.4 |
| · | · | · | · | · | · | · |
| Italy | Male | 7 | 130 | A | 36.7 | 0.3 |
| · | · | · | · | · | · | · |
| Italy | Female | 40 | 175 | B | 36.0 | 0.4 |
| · | · | · | · | · | · | · |

INFORMATION MONITORING DEVICE, INFORMATION MANAGEMENT SYSTEM, IMMIGRATION INSPECTION METHOD, ADMISSION MANAGEMENT METHOD, AND COMPUTER-READABLE RECORDING MEDIUM STORING INFORMATION MANAGEMENT PROGRAM

CROSS-REFERENCE TO RELATED APPLICATIONS

This is a continuation-in-part application of PCT International Application No. PCT/JP2021/020966 filed on Jun. 2, 2021, designating the United States of America, which is based on and claims priority of Japanese Patent Application No. 2020-110146 filed on Jun. 26, 2020. The entire disclosures of the above-identified applications, including the specifications, drawings and claims are incorporated herein by reference in their entireties.

TECHNICAL FIELD

The present invention relates to an information monitoring device that monitors detected information, as well as an information management system, an immigration inspection method, an admission management method, and a computer-readable recording medium storing an information management program, which use the information monitoring device.

BACKGROUND ART

A system, in which a temperature sensor is attached to a human body by an adhesive patch to measure a body temperature and the measured temperatures are accumulated, has been conventionally known (see Patent Literature (PTL) 1, for example).

CITATION LIST

Patent Literature

PTL 1: Japanese Unexamined Patent Application Publication (Translation of PCT Application) No. 2009-535141

SUMMARY OF INVENTION

According to a technique disclosed in PTL 1, a user can freely peel off or re-paste the temperature sensor. Thus, if a third parson tries to check the measured body temperatures at a later date, the body temperatures that are not necessarily measured continuously for a certain period of time are accumulated.

A purpose of the present invention is to provide an information monitoring device being able to easily confirm that detected information corresponds to continuously detected information, an information management system, an immigration inspection method, an admission management method, and a computer-readable recording medium storing an information management program.

An information monitoring device according to an aspect of the present invention is an information monitoring device for monitoring information, which includes a sensor that detects predetermined target information from a measurement target; a detection controller that performs control on the sensor so that the sensor repeatedly detects the target information; a holding member that attaches the sensor to the measurement target to hold the sensor; and a removal detector that detects removal of the sensor from the measurement target.

An information management system according to an aspect of the present invention includes the information monitoring device described above; a storage that stores information; and a storage processor that causes the storage to cumulatively store the target information repeatedly detected.

An information management system according to an aspect of the present invention includes a storage that stores information obtained from the information monitoring device described above; and a storage processor that causes the storage to cumulatively store the target information repeatedly detected.

An immigration inspection method according to an aspect of the present invention uses the information management system described above. In the method, when a person who wears the information monitoring device enters a country, an immigration inspection or quarantine is performed based on the information block obtained by the terminal.

An immigration inspection method according to an aspect of the present invention uses the information management system described above. The method includes selling the information monitoring device as a ticket; and determining, at admission of a person wearing the information monitoring device, whether the admission is allowed, based on the information block obtained by the terminal.

A computer-readable recording medium storing an information management program according to an aspect of the present invention causes a computer to function as a storage that stores information obtained by the information monitoring device described above; and a storage processor that causes the storage to cumulatively store the target information repeatedly detected.

BRIEF DESCRIPTION OF DRAWINGS

These and other advantages and features will become apparent from the following description thereof captured in conjunction with the accompanying Drawings, by way of non-limiting examples of embodiments disclosed herein.

FIG. 5 is a block diagram showing an example of each electrical configuration of a circuit shown in FIG. 2 and a wireless communication terminal shown in FIG. 1.

FIG. 11 is an explanatory diagram showing an example of a diagnosis criterion table stored in a storage in advance.

DESCRIPTION OF EMBODIMENTS

Figure 1:
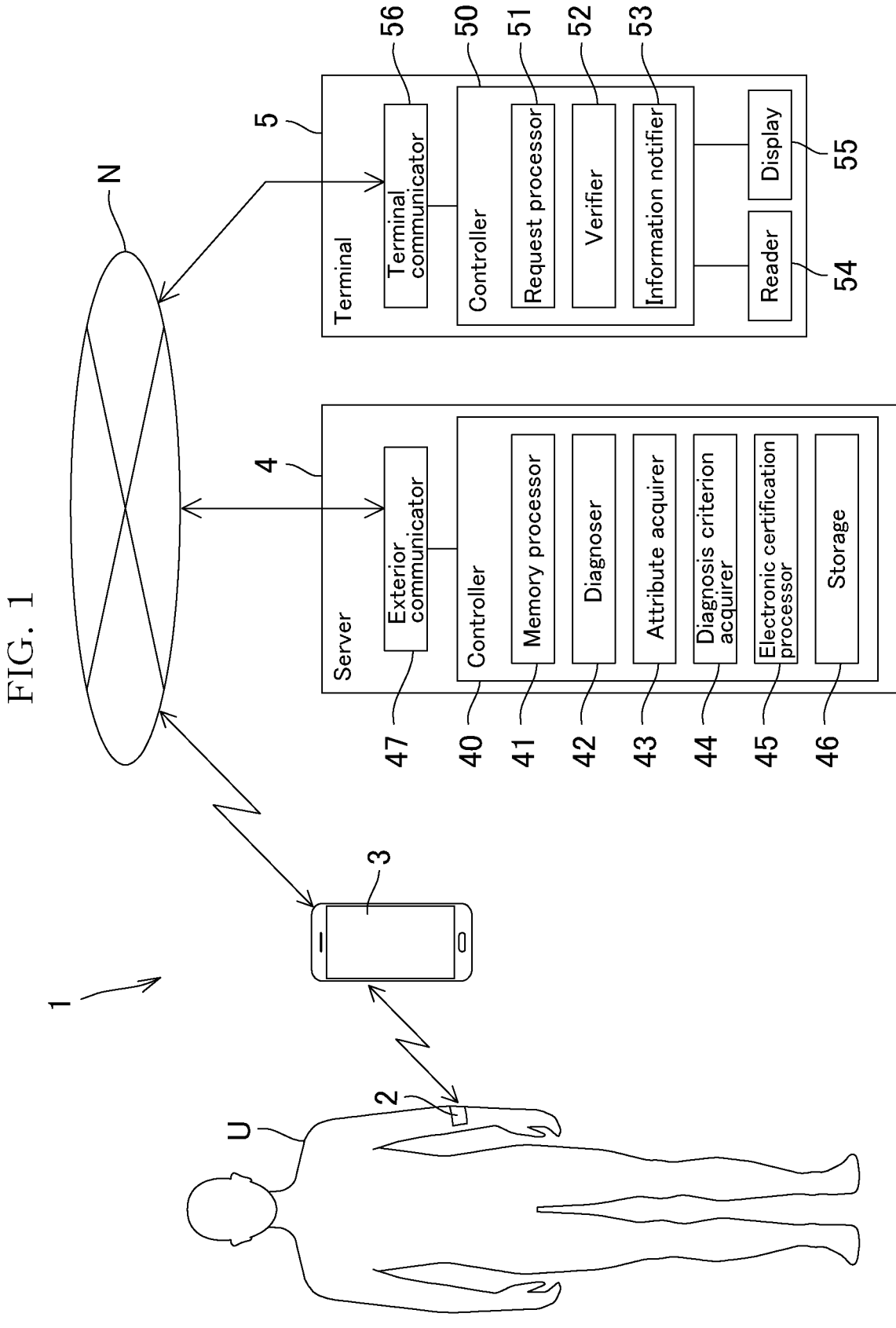
FIG. 1 is a block diagram showing an example of a configuration of an information management system according to an embodiment of the present invention.

Hereinafter, embodiments of the present invention are described with reference to the drawings. It should be noted that same reference numerals in each drawing indicate the same configuration, and the description thereof is omitted.

FIG. 1 is a block diagram showing an example of a configuration of an information management system according to an embodiment of the present invention. An information management system 1 shown in FIG. 1 includes an information monitoring device 2, a wireless communication terminal 3, a server 4, and a terminal 5. The wireless communication terminal 3, the server 4, and the terminal 5 are communicably connected via a network N in a data transmittable/receivable manner.

The information monitoring device 2 is used by being pasted and attached to a body of a person U who is a measurement target. For the wireless communication terminal 3, a smartphone used by the person U can be preferably used. It is assumed that the terminal 5 is used, for example, for an immigration inspection and quarantine at an immigration office, and for admission reception of various venues such as event venues, concert venues, stadiums, movie theaters, theaters, and so on.

The network N may include various networks, such as a mobile wireless communication base station, a wide area network (WAN), a local area network (LAN), and the Internet.

The wireless communication terminal 3 is, for example, a wireless terminal, such as a smartphone, a tablet terminal, a portable personal computer, and so on. The wireless communication terminal 3 is wirelessly communicable with the information monitoring device 2 by means of relatively short-range wireless communication means, such as Bluetooth (registered trademark). In addition, the wireless communication terminal 3 can access the network N through mobile communication or wireless communication such as WiFi (registered trademark), and can perform transmitting/receiving to/from the server 4 via the network N. The wireless communication terminal 3 relays data communication between the information monitoring device 2 and the server 4.

Figure 2:
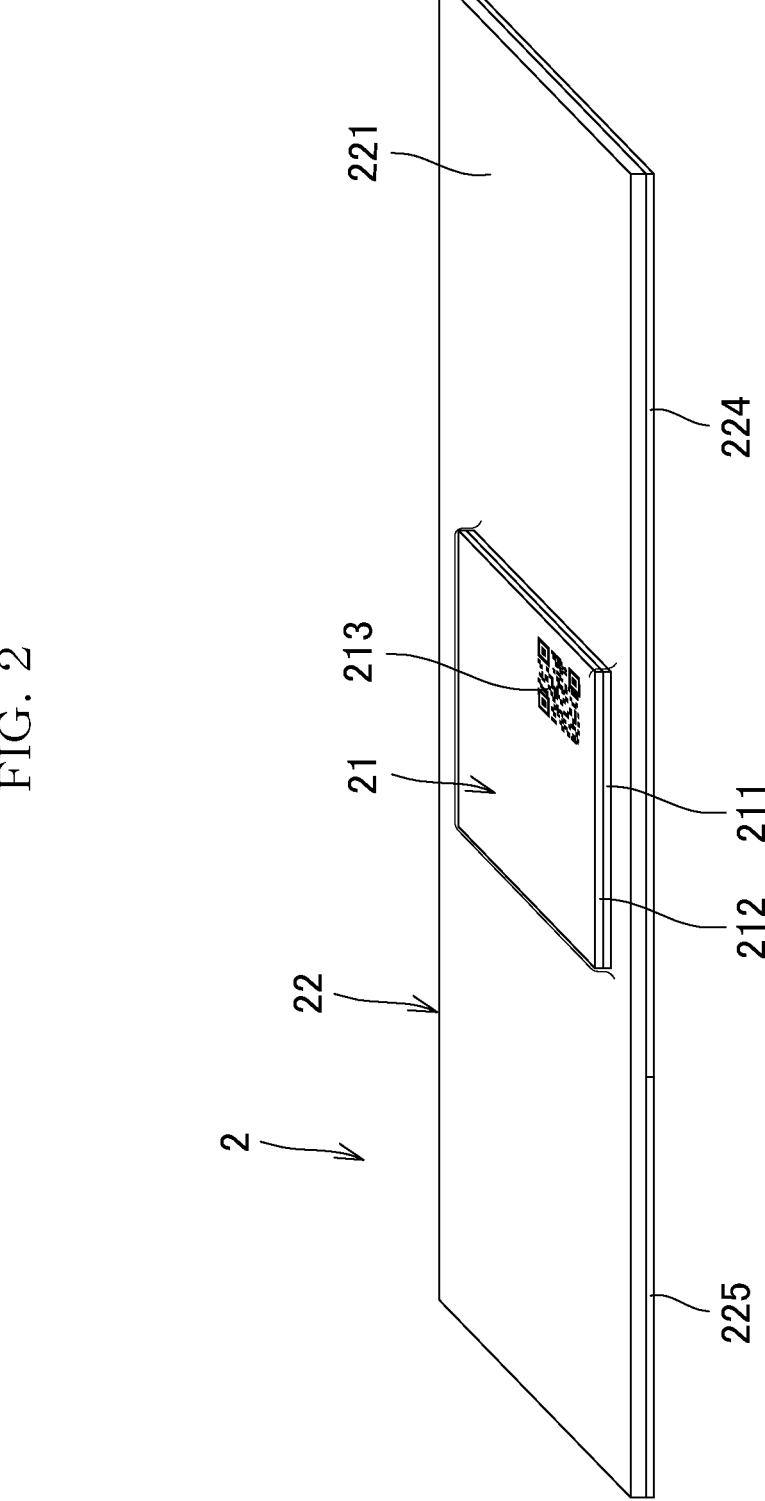
FIG. 2 is a perspective view of an information monitoring device shown in FIG. 1, seen from a front side.
Figure 3:
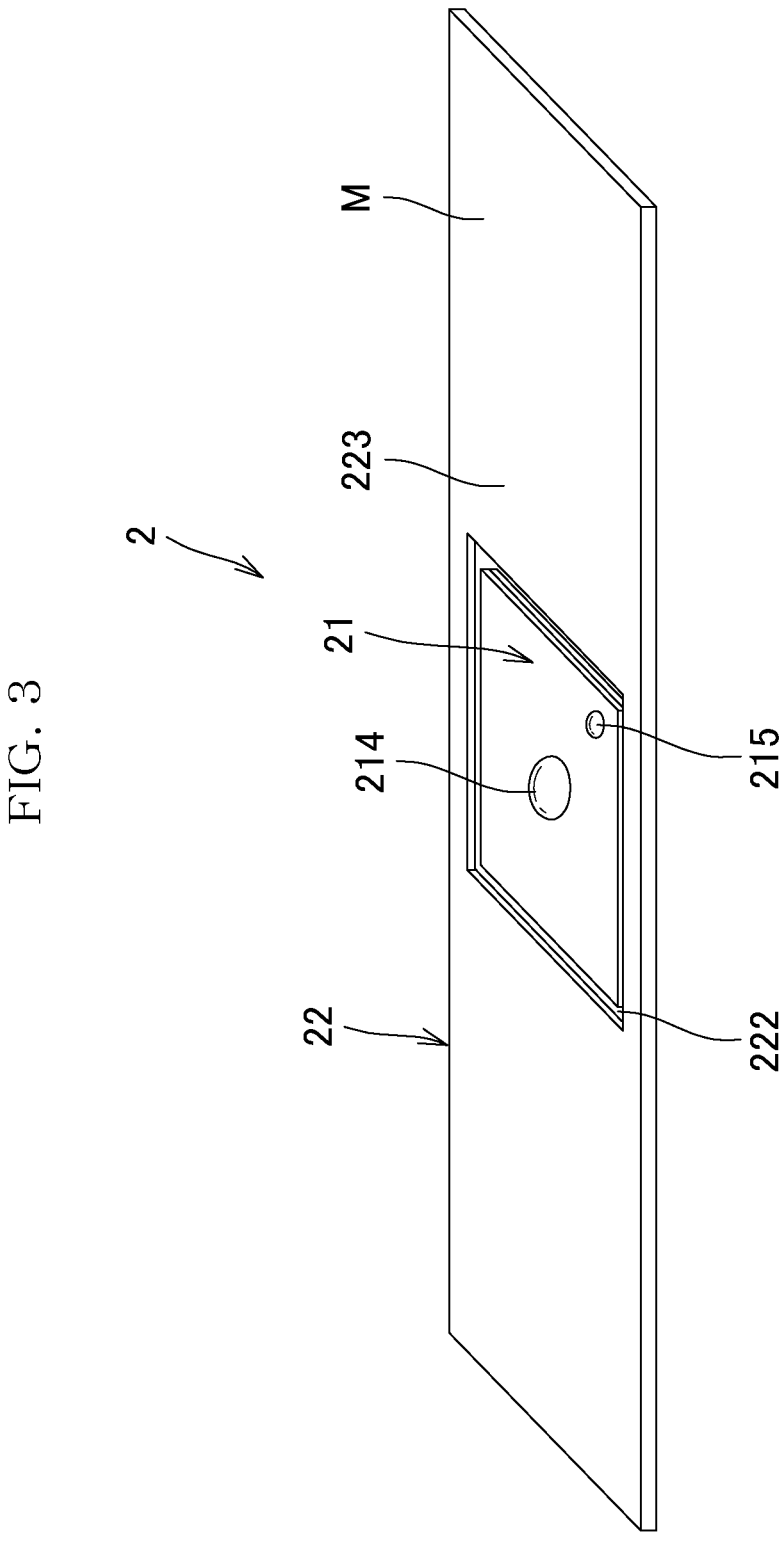
FIG. 3 is a perspective view of the information monitoring device shown in FIG. 2, seen from a back side.
Figure 4:
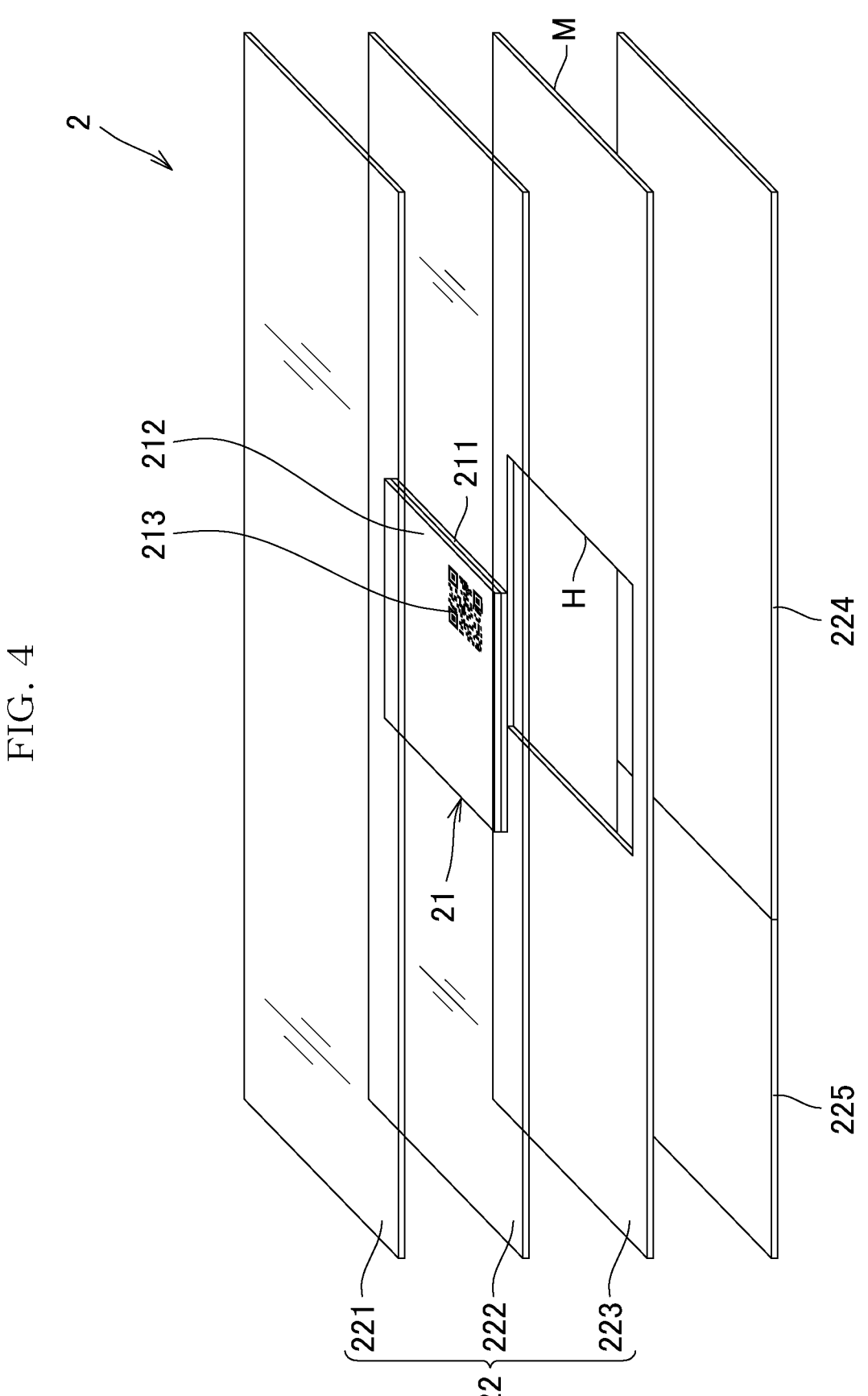
FIG. 4 is an exploded perspective view of the information monitoring device shown in FIG. 2.

FIG. 2 is a perspective view of the information monitoring device 2 shown in FIG. 1, seen from a front side. FIG. 3 is a perspective view of the information monitoring device 2 shown in FIG. 2, seen from a back side. FIG. 4 is an exploded perspective view of the information monitoring device 2 shown in FIG. 2.

The information monitoring device 2 includes a circuit 21 and a holding member 22 that holds the circuit 21. The circuit 21 has a rectangular plate shape, for example. The holding member 22 is configured by stacking, for example, a cover sheet 221 (sheet member), an under sheet 222 (sheet member), and an adhesive layer 223, in this order. The circuit 21 is inserted between the cover sheet 221 and the under sheet 222, so as to be held.

The cover sheet 221 and the under sheet 222 are transparent sheet members, for example, having a light-transmitting property and a waterproof property. For the cover sheet 221 and the under sheet 222, a resin sheet, such as a polyester film, can be used, for example. The cover sheet 221 and the under sheet 222 are welded by heat or adhered by glue, for example. Accordingly, the circuit 21 is hermetically sealed to have waterproofness against perspiration, rain, hand washing, bathing, and so on.

The cover sheet 221 and the under sheet 222 are not limited to be stacked. The holding member 22 may include only one of the cover sheet 221 and the under sheet 222.

The adhesive layer 223 is provided with an opening H that opens to avoid the circuit 21. The adhesive layer 223 is used to paste the information 5 monitoring device 2 to the body of a person U.

Before the information monitoring device 2 is pasted to the body of the person U, releasable sheets 224 and 225 are attached to an attachment surface M of the adhesive layer 223. Each of the releasable sheets 224 and 225 has a light blocking effect. Surfaces of the releasable sheets 224 and 225 are processed so as to be easily separated from the adhesive layer 223. The releasable sheets 224 and 225 are separated so as to be easily peeled off from the attachment surface M.

The circuit 21 is configured by stacking a circuit board 211 having a substantially rectangular plate shape and a battery 212 having a sheet shape. It should be noted that the circuit board 211 and the battery 212 are not limited to being stacked, and various arrangements for them can be adopted.

A two-dimensional code, such as a QR code (registered trademark) or an image code 213, such as a bar code, is printed on a surface of the circuit 21. Each information monitoring device 2 is provided with an identification information ID for identifying itself from other information monitoring devices 2. The image code 213 contains information that indicates the identification information ID provided to the information monitoring device 2 in which the circuit 21 is included. The cover sheet 221 has a translucent property, and thus the image code 213 can be read from the outside through the cover sheet 221.

A temperature sensor 214 and an optical sensor 215 are arranged on a rear surface of the circuit 21. The information monitoring device 2 is pasted and attached to a person to cause the temperature sensor 214 to be in close contact with the body of the person U via the under sheet 222. With this configuration, the temperature sensor 214 detects a body temperature T of the person U.

When the releasable sheet 224 is pasted on the attachment surface M of the adhesive layer 223, the optical sensor 215 is blocked from light by the releasable sheet 224 and does not detect the light. When the releasable sheet 224 is peeled off from the attachment surface M, the optical sensor 215 detects light in a surrounding environment through the under sheet 222 having the light-transmitting property. When the attachment surface M of the information monitoring device 2 is attached to the person U, the optical sensor 215 is shielded from the light in the surrounding environment and does not detect the light.

In other words, the optical sensor 215 does not detect light in a surrounding environment while the information monitoring device 2 is attached to a person U, and when the information monitoring device 2 is peeled off from the person U, the light in the surrounding environment enters the optical sensor 215 and is detected. Accordingly, the optical sensor 215 can detect that the temperature sensor 214 of the information monitoring device 2 is removed from the person U and the information monitoring device 2 is separated from the person U. The optical sensor 215 corresponds to an example of a removal detector.

The information monitoring device 2 can detect the body temperatures T of a person U by means of the temperature sensor 214 while being attached to the person U. Accordingly, if the optical sensor 215 detects no separation of the information monitoring device 2 from the person U, it is easily confirmed that the body temperatures T (information) have been continuously detected after the detection of the body temperature T (information) was started.

Figure 5:
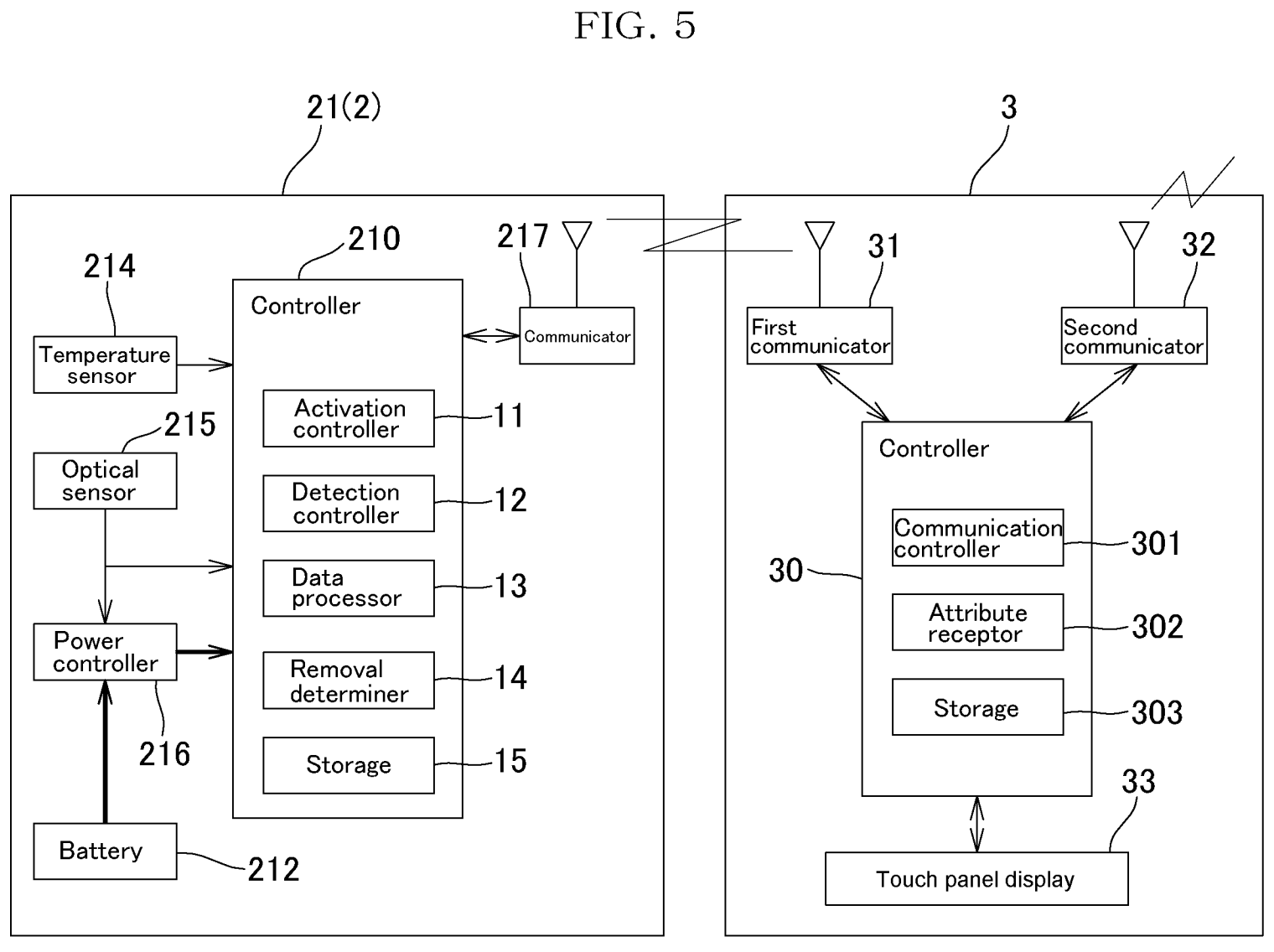

FIG. 5 is a block diagram showing an example of each electrical configuration of the circuit 21 shown in FIG. 2 and the wireless communication terminal 3 shown in FIG. 1. The circuit 21 includes a battery 212, the temperature sensor 214 (sensor), the optical sensor 215, a power controller 216, a communicator 217, and a controller 210.

The temperature sensor 214 is a temperature sensor for measuring a body temperature T (target information) of a person U, and outputs a signal indicating the detected temperature to the controller 210. The optical sensor 215 detects light in a surrounding environment, and outputs a detection signal indicating the detected light to the power controller 216 and the controller 210.

The power controller 216 is configured using, for example, a transistor, a latch circuit, and so on. A light detection level DL indicated by the detection signal from the optical sensor 215 may exceed an on-level Lon previously set as a level indicating that the light in the surrounding environment is detected. In other words, predetermined light is detected by the optical sensor 215. At this time, the power controller 216 causes the battery 212 to start supplying power to each part in the circuit 21.

The communicator 217 is a communication interface circuit that is communicable with the wireless communication terminal 3. As a communication method of the communicator 217, Bluetooth (registered trademark) with low power consumption, for example, can be preferably used.

The controller 210 is a so-called microcomputer that is configured by, for example, a central processing unit (CPU) that performs a predetermined logical calculation; a random access memory (RAM) that temporarily stores data; a storage element, such as a non-volatile flash memory; a real time clock (RTC); their peripheral circuits; and so on.

The controller 210 executes a predetermined program stored in the storage element in advance, so as to function as an activation controller 11, a detection controller 12, a data processor 13, and a removal determiner 14. The RAM and/or the storage element described above functions as the storage 15.

The storage 15 stores in advance an identification information ID assigned to the information monitoring device 2 in which the storage 15 is included, i.e., the identification information ID same as an identification information ID indicated by its own image code 213.

The detection level DL indicated by the detection signal from the optical sensor 215 may be lower than an off-level Loff indicating that predetermined light is not detected, i.e., the predetermined light may be no longer detected, after the predetermined light is detected by the optical sensor 215 and the power supply by the battery 212 is started to activate the controller 210 (i.e., after the predetermined light is detected by the optical sensor 215). At such a moment, the activation controller 11 causes the communicator 217, the detection controller 12, the data processor 13, and the removal determiner 14 to start operating.

The detection controller 12 repeatedly obtains the body temperatures T detected by the temperature sensor 214, at a predetermined detection interval tw. In other words, the detection controller 12 causes the temperature sensor 214 to repeatedly detect the body temperatures T.

Further, the detection controller 12 shortens the detection interval tw, when the body temperature T corresponds to a specific phenomenon previously set as a phenomenon that may be abnormal, e.g., the body temperature T exceeds 37° C., for example.

The data processor 13 causes the communicator 217 to transmit the body temperature T obtained by the detection controller 12; date and time information indicating the date and time of the detection; and its own identification information ID, in association with one another, to the wireless communication terminal 3. It should be noted that the data processor 13 may cause the storage 15 to cumulatively store and accumulate the body temperatures T in association with the date and time information, and may cause the communicator 217 to collectively transmit the accumulated data to the wireless communication terminal 3, when the accumulated data accumulates to some extent.

When the detection level DL is lower than the off-level Loff, i.e., the predetermined light is not detected, after the power supply from the battery 212 is started to activate the controller 210 (i.e., after the predetermined light is detected by the optical sensor 215), and then the detection level DL exceeds the on-level Lon again, i.e., the optical sensor 215 detects the predetermined light, the removal determiner 14 determines that the temperature sensor 214 of the information monitoring device 2 is removed from the person U, and performs notification by causing the communicator 217 to transmit removal information indicating the removal of the information monitoring device 2 to the wireless communication terminal 3.

The on-level Lon and the off-level Loff may respectively be at detection levels of the same brightness, or the off-level Loff may be at a darker detection level than that of the on-level Lon.

It should be noted that the removal determiner 14 is not limited to performing the notification of the removal information by communication. For example, if an indicator such as a light emitting diode (LED) is provided on the front side of the circuit 21, and the removal determiner 14 determines that the temperature sensor 214 of the information monitoring device 2 has been removed from the person U, the removal information may be notified by being displayed, e.g., by keeping the LED on.

The wireless communication terminal 3 includes a first communicator 31, a second communicator 32, a touch panel display 33, and a controller 30. The first communicator 31 is a communication circuit that is wirelessly communicable with the communicator 217 of the information monitoring device 2, and is, for example, a communication interface circuit for Bluetooth (registered trademark). The second communicator 32 is a communication circuit that is wirelessly communicable with the server 4 via the network N, and is, for example, a communication interface circuit for a mobile communication, WiFi (registered trademark), and so on.

The controller 30 is a so-called microcomputer that is configured by, for example, a CPU that performs a predetermined logical calculation; a RAM that temporarily stores data; a storage element, such as a non-volatile flash memory; an RTC; their peripheral circuits; and so on.

The controller 30 executes a predetermined program stored in a storage element in advance, so as to function as a communication controller 301 and an attribute receptor 302. The RAM and/or the storage element of the controller 30 functions as a storage 303. The program may be downloadable from the network N as a so-called app.

The communication controller 301 causes the second communicator 32 to transmit, to the server 4 via the network N, body temperatures T, date and time information, and an identification information ID, which are received by the first communicator 31 from the information monitoring device 2. The communication controller 301 causes the storage 303 to cumulatively store the body temperatures T, date and time information, and identification information ID, which are received by the first communicator 31, and to cause the second communicator to collectively transmit the data, to the server 4, when the accumulated data accumulates to some extent.

Hereinafter, the fact that communication controller 301 causes the first communicator 31 to perform transmitting/receiving to/from the information monitoring device 2 may be simply described as the communication controller 301 performing transmitting/receiving to/from the information monitoring device 2. The fact that the communication controller 301 causes the second communicator 32 to transmit/receive data to/from the server 4 via the network N may be simply referred to as the communication controller 301 transmitting/receiving data to/from the server 4.

Further, when receiving the removal information from the information monitoring device 2, the communication controller 301 transmits the removal information to the server 4.

The attribute receptor 302 accepts input of attribute information from a person U. The attribute information represents, for example, the attributes of the person U, such as nationality, gender, age, height, weight, and a blood type.

The communication controller 301 transmits the attribute information accepted by the attribute receptor 302 to the server 4, in association with the identification information ID of the information monitoring device 2 of the person U.

Referring to FIG. 1, the server 4 includes an external communicator 47 and a controller 40. The external communicator 47 is a communication interface circuit that is communicable with the second communicator 32 of the wireless communication terminal 3 via the network N. The external communicator 47 receives information that is transmitted from the communicator 217 of the information monitoring device 2 and is relayed by the wireless communication terminal 3, so as to receive the information indirectly from the communicator 217.

The controller 40 is a so-called microcomputer that is configured by, for example, a CPU that executes a predetermined logical calculation; a RAM that temporarily stores data; a storage device such as a non-volatile hard disk drive (HDD) and a solid state drive (SDD); an RTC; their peripheral circuits; and so on.

The controller 40 executes an information management program stored in the storage element in advance, so as to function as a storage processor 41, a diagnoser 42, an attribute acquirer 43, a diagnosis criterion acquirer 44, and an electronic certification processor 45. The RAM and/or the storage device of the controller 40 functions as a storage 46. The information management program may be stored in a storage medium.

In the storage 46, a diagnosis criterion table, which indicates the correspondence between the attribute information and diagnosis criteria, is statistically obtained and stored in advance, for example.

The storage processor 41 associates, with one another, the body temperature T, the date and time information, and the identification information ID, which are received by the external communicator 47 from the communicator 217 of the information monitoring device 2 via the wireless communication terminal 3, and causes the storage 46 to store them cumulatively. The storage processor 41 thus causes the storage 46 to store a plurality of body temperatures T and a plurality of pieces of date and time information, which are respectively associated with the identification information ID, as a group of information blocks. The information blocks may be so-called data files.

When receiving the removal information from the wireless communication terminal 3, the storage processor 41 causes the storage 46 to store the removal information as well in the information block.

The attribute acquirer 43 obtains the attribute information and the identification information ID which are sent from the wireless communication terminal 3, in association with each other, and causes the storage 46 to store them.

The diagnosis criterion acquirer 44 obtains diagnosis criterion that serves as criterion for diagnosis, based on the attribute information stored in the storage 46.

The diagnoser 42 performs a diagnosis, based on the body temperatures T stored in the storage 46, with using the diagnosis criterion obtained by the diagnosis criterion acquirer 44. The diagnoser 42 also determines a fever type based on the body temperatures T stored in the storage 46.

The electronic certification processor 45 obtains an electronic certificate; causes the storage 46 to store the electronic certificate; provides an electronic signature to the information block stored in the storage 46; associates the information block provided with the electronic signature with the identification information ID; and causes the storage 46 to store the associated information block and identification information ID. The electronic certificate processor 45 can obtain the electronic certificate by accessing a certificate authority of a third party (not shown) connected to the network N.

The terminal 5 is configured using, for example, a personal computer, a tablet terminal, and so on. The terminal 5 includes a controller 50, a reader 54, a display 55, and a terminal communicator 56.

The terminal communicator 56 is a communication interface circuit that is communicable with the external communicator 47 of the server 4 via the network N. The display 55 is a display device, such as a liquid crystal panel and an organic electroluminescence (EL) panel.

The reader 54 is a reading device that reads the identification information ID from the information monitoring device 2. As the reader 54, a camera that reads the identification information ID from the image code 213 can be used, for example.

The controller 50 is a so-called microcomputer that is configured by, for example, a CPU that executes a predetermined logical calculation; a RAM that temporarily stores data; a storage device such as a non-volatile HDD or a solid state drive (SDD); an RTC; their peripheral circuits; and so on.

The controller 50 executes a predetermined program stored in the storage device in advance, so as to function as a request processor 51, a verifier 52, and an information notifier 53.

The request processor 51 causes the terminal communicator 56 to transmit, to the server 4 via the network N, a request of the information block associated with an identification information ID, based on the identification information ID read by the reader 54. Hereinafter, the fact that the request processor 51 or the verifier 52 causes the terminal communicator 56 to perform transmitting/receiving to/from the server 4 via the network N may be simply described as the request processor 51 or the verifier 52 performing transmitting/receiving to/from the server 4.

In the server 4 that has received the request, the storage processor 41 refers to the storage 46, and transmits, to the terminal 5, the electronic certificate and the information block that is assigned with the electronical signature and associated with the identification information ID.

In the terminal 5, the verifier 52 verifies the information block assigned with the electronical signature, based on the electronic certificate.

The information notifier 53 performs notification by, for example, displaying the information of the information block on the display 55. Further, when the verifier 52 fails verification, i.e., when there is a possibility that the information block has been tampered with, the information notifier 53 notifies the verification failure by performing display on the display 55 or the like.

As a result, a user of the terminal 5 can check information in the information block of the person U to whom the information monitoring device 2 of the identification information ID is attached, from the display on the display 55 or other means, and can check whether there is a possibility that the information of the information block has been tampered with.

Further, if the information monitoring device 2 is removed from the person U within a previously set monitoring period tm, the information block contains the removal information. In view of this, the user of the terminal 5 can confirm whether records of body temperatures T contained in an information block within the monitoring period tm were continuously measured without removal of the information monitoring device 2. This improves the certainty in monitoring the body temperatures T over the monitoring period tm.

Figure 6:
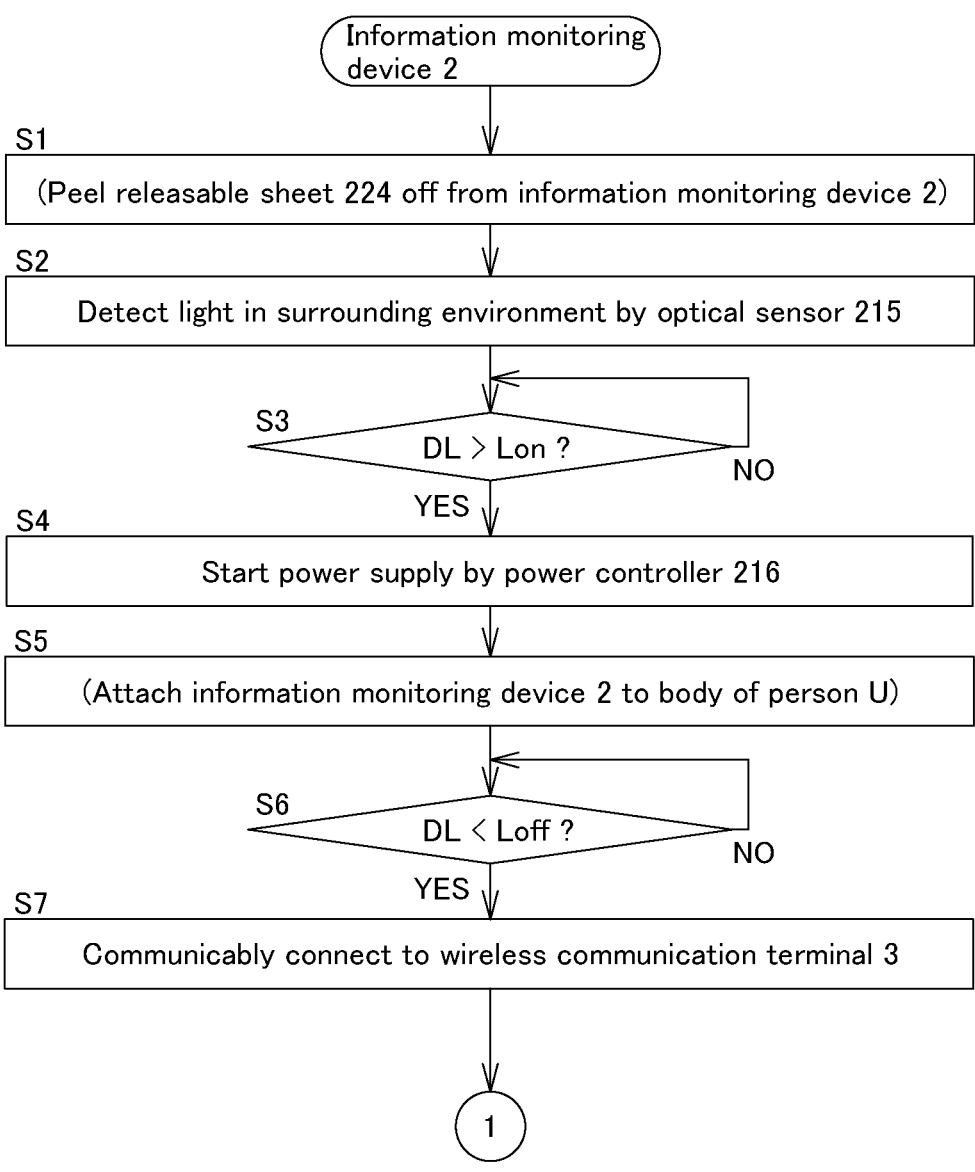
FIG. 6 is a flowchart showing an example of an operation of the information monitoring device shown in FIG. 1.
Figure 7:
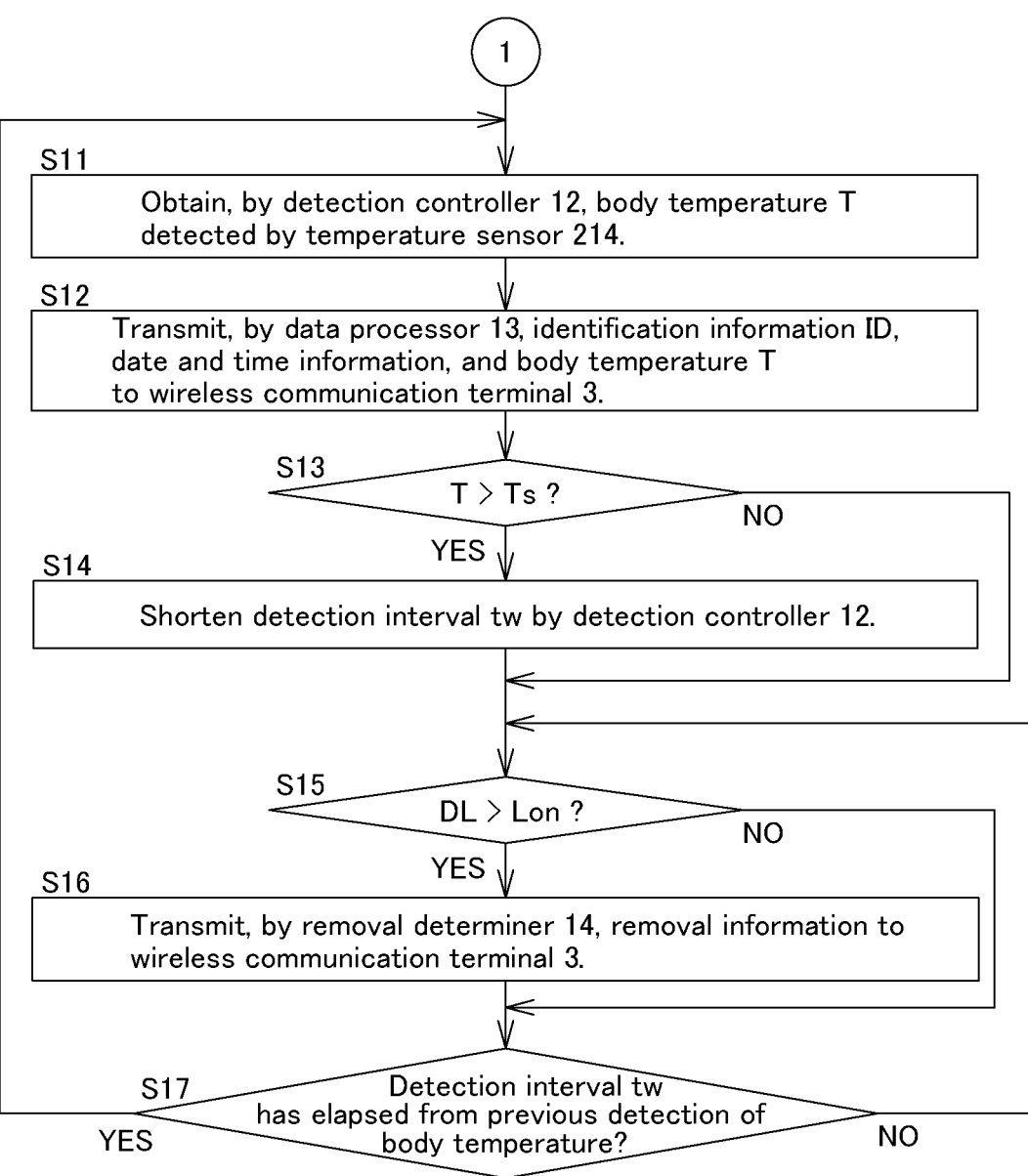
FIG. 7 is a flowchart showing an example of the operation of the information monitoring device shown in FIG. 1.

Next, an example of the operation when the information management system 1 is applied to an immigration inspection is described. FIGS. 6 and 7 are flowcharts each showing an example of the operation of the information monitoring device 2. First, a person U who intends to travel from country A to country B obtains the information monitoring device 2.

Then, the person U peels off the releasable sheet 224 from the information monitoring device 2 (Step S1). The releasable sheet is separated into the releasable sheet 224 and the releasable sheet 225. Accordingly, the person U can hold a part of the releasable sheet, at which the releasable sheet 225 is pasted, and peel off the releasable sheet 224. This makes it easier to peel off the releasable sheet 224 from the information monitoring device 2.

When the releasable sheet 224 is peeled off from the information monitoring device 2, the optical sensor 215 is no longer shielded from light in a surrounding environment. Thus, the optical sensor 215 detects the light in the surrounding environment (Step S2).

Then, when the detection level DL of the optical sensor 215 exceeds the on-level Lon, i.e., when predetermined light is detected (YES in Step S3), the power controller 216 causes the battery 212 to start supplying power to the controller 210, the temperature sensor 214, and the communicator 217 (Step S4).

Accordingly, the power supply from the battery 212 can be interrupted until the releasable sheet 224 is peeled off from the information monitoring device 2. This reduces the possibility that the battery 212 is consumed while the information monitoring device 2 is kept without being used.

Next, the person U pastes the adhesive layer 223 that corresponds to the part where the releasable sheet 224 is peeled off, to his/her body, and then peels off the releasable sheet 225 so as to paste the entire adhesive layer 223 to the body of the person U. As a result, the information monitoring device 2 is attached to the body of the person U (Step S5).

As described above, holding a part where the releasable sheet 225 is not peeled off, the adhesive layer 223 on a part where the releasable sheet 224 is peeled off is pasted to the body of the person U. Then, the releasable sheet 225 can be peeled off and the entire adhesive layer 223 can be pasted to the body of the person U. Thus, it is easy to attach the information monitoring device 2 to the body of the person U.

When the information monitoring device 2 is attached to the body of the person U, the temperature sensor 214 and the optical sensor 215 are in close contact with the body of the person U via the under sheet 222.

When the optical sensor 215 is in close contact with the body of the person U, light in a surrounding environment does not enter the optical sensor 215. As a result, the detection level DL of the optical sensor 215 is lower than the off-level Loff, i.e., the predetermined light is no longer detected (YES in Step S6). At this time, the activation controller 11 causes the communicator 217, the detection controller 12, the data processor 13, and the removal determiner 14 to start operations. As a result, processing in Step S7 and subsequent steps are started.

The releasable sheet 225 is peeled off, and the light in the surrounding environment is detected by the sensor 215, allowing the battery 212 to start power supply. Then, the information monitoring device 2 is attached to the body of the person U, and the temperature sensor 214 can detect the body temperature T. Thus, according to the activation controller 11, the body temperature T is obtained after waiting until this stage. Accordingly, it is possible to reduce the possibility that an environmental temperature or the like is erroneously detected as the body temperature T before the information monitoring device 2 is attached to the body of the person U.

Next, the communicator 217 performs communication connection processing for enabling communication with the wireless communication terminal 3 (Step S7).

Figure 8:
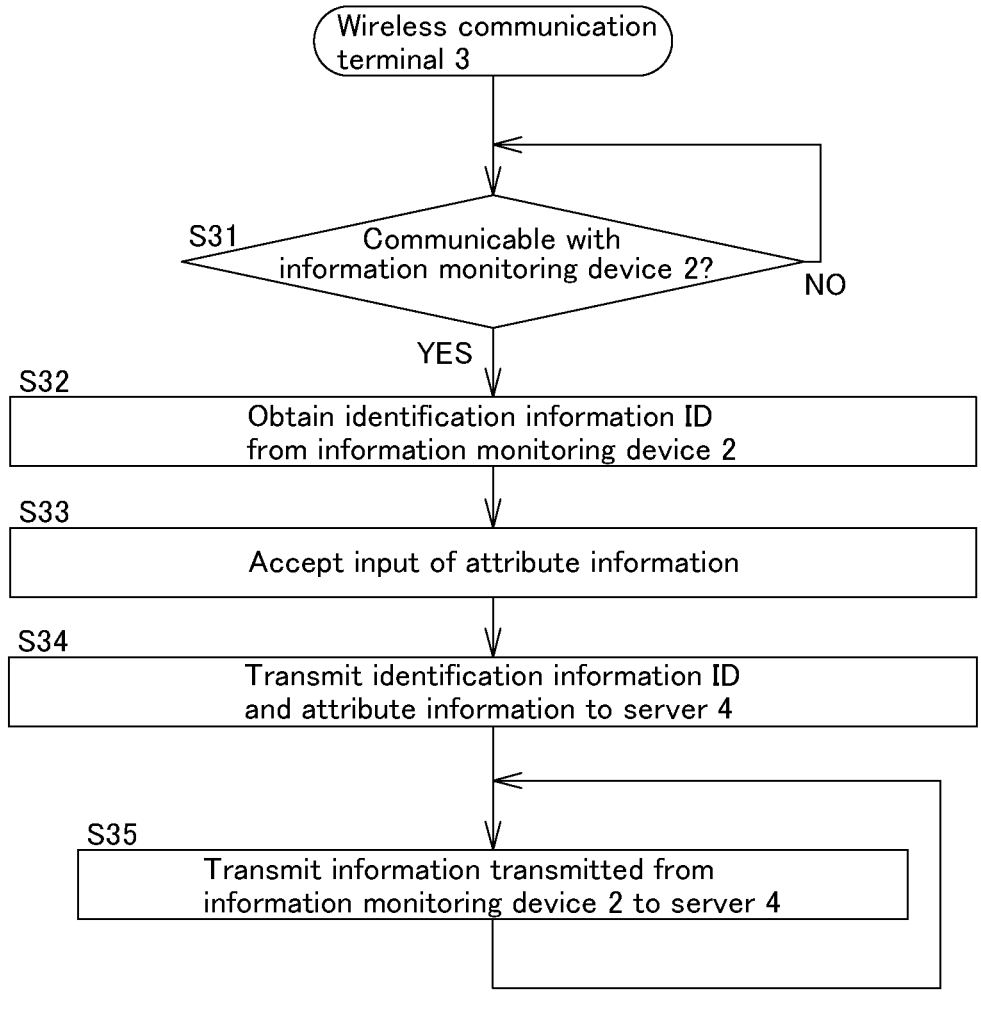
FIG. 8 is a flowchart showing an example of an operation of the wireless communication terminal shown in FIG. 1.

FIG. 8 is a flowchart showing an example of an operation of the wireless communication terminal 3. The communication controller 301 performs communication connection processing with respect to the information monitoring device 2. When the communication becomes possible (YES in Step S31), the communication controller 301 receives the identification information ID from the information monitoring device 2 (Step S32), and the attribute receptor 302 accepts input of the attribute information relating to the person U (Step S33).

The attribute receptor 302 displays, for example, on the touch panel display 33, a message that prompts input of the attribute information. For example, "Please enter your nationality, gender, age, height, weight, and a blood type". The attribute receptor 302 accepts attribute information inputted by the person U operating the touch panel display 33.

The attribute receptor 302 transmits the attribute information obtained as described above to the server 4 in association with the identification information ID obtained from the information monitoring device 2 (Step S34).

Thereafter, the wireless communication terminal 3 transmits the information transmitted from the information monitoring device 2 to the server 4, and relays communication between the information monitoring device 2 and the server 4 (Step S35). Thus, the information monitoring device 2 can transmit information to the remote server 4 using the communicator 217 that uses a communication method with a short communication distance and low power consumption, such as Bluetooth (registered trademark). Therefore, the power consumption and the cost of the information monitoring device 2 can be easily reduced.

With reference to FIG. 7, in the information monitoring device 2, the temperature sensor 214 detects body temperatures T of the person U, and the detection controller 12 obtains the detected body temperatures T (Step S11).

Next, the data processor 13 transmits, to the wireless communication terminal 3, the body temperature T obtained by the detection controller 12, date and time information indicating the date and time when the body temperature T was obtained, and the identification information ID, in association with one another (Step S12).

Then, in the wireless communication terminal 3, the body temperature T, the date and time information, and the identification information ID are transmitted to the server 4 by the communication controller 301 (Step S35).

Next, in the information monitoring device 2, the detection controller 12 compares the body temperature T with a previously set specific body temperature Ts (Step S13). The specific body temperature Ts can be, for example, 37.0° C. as a body temperature that may cause fever, which is an example of an abnormality.

When the body temperature T exceeds the specific body temperature Ts (YES in Step S13), the detection controller 12 shortens the detection interval tw than the present interval (Step S14), and allows the processing to proceed to Step S15. On the other hand, if the body temperature T does not exceed the specific body temperature Ts (NO in Step S13), the present detection interval tw is maintained without performing processing in Step S14, and processing proceeds to Step S15.

A body temperature T exceeding the specific body temperature Ts (for example, 37.0° C.) is an event that may be abnormal and corresponds to an example of a specific phenomenon. It should be noted that the specific body temperature Ts is not limited to 37.0° C., and may be appropriately set according to a monitoring purpose of the information monitoring device.

If the detection interval tw is shortened, a frequency in detecting the body temperature T is increased by processing in Step S17 described later. Thus, the detection frequency of the body temperature T is increased at a time when there is a high possibility of an abnormality, thereby improving the accuracy in monitoring the body temperature T, with reducing the detection frequency in the body temperature T or a communication frequency to reduce the power consumption and communication load.

Next, in Step S15, the removal determiner 14 compares the detection level DL and the on-level Lon, of the optical sensor 215 (Step S15). If the detection level DL exceeds the on-level Lon (YES in Step S15), the removal determiner 14 transmits, to the wireless communication terminal 3, the removal information indicating that the information monitoring device 2 has been removed from the person U, together with the identification information ID (Step S16).

Then, in the wireless communication terminal 3, the communication controller 301 transmits the removal information and the identification information ID to the server 4 (Step S35).

The fact that the detection level DL exceeds the on-level Lon (YES in Step S15) means that the optical sensor 215 has detected light. It can be assumed that the information monitoring device 2 has been removed from the person U and the light from an external environment enters the optical sensor 215. Therefore, if the detection level DL exceeds the on-level Lon (YES in Step S15), the removal information is transmitted to the wireless communication terminal 3 (Step S16), thereby notifying, to the server 4 via the wireless communication terminal 3, that the monitoring device 2 has been removed from the person U.

Next, the detection controller 12 confirms whether the detection interval tw has elapsed from the previous detection of the body temperature T in Step S11 (Step S17). If the detection interval tw has not elapsed yet (NO in Step S17), processing in Steps S15 to S17 is repeated to monitor the removal of the information monitoring device 2 from the person U.

On the other hand, if the detection interval tw has elapsed (YES in Step S17), processing in Steps S11 to S17 is repeated again. Accordingly, the body temperatures T can be continuously detected at the detection interval tw, and continuously transmitted to the server 4.

Figure 9:
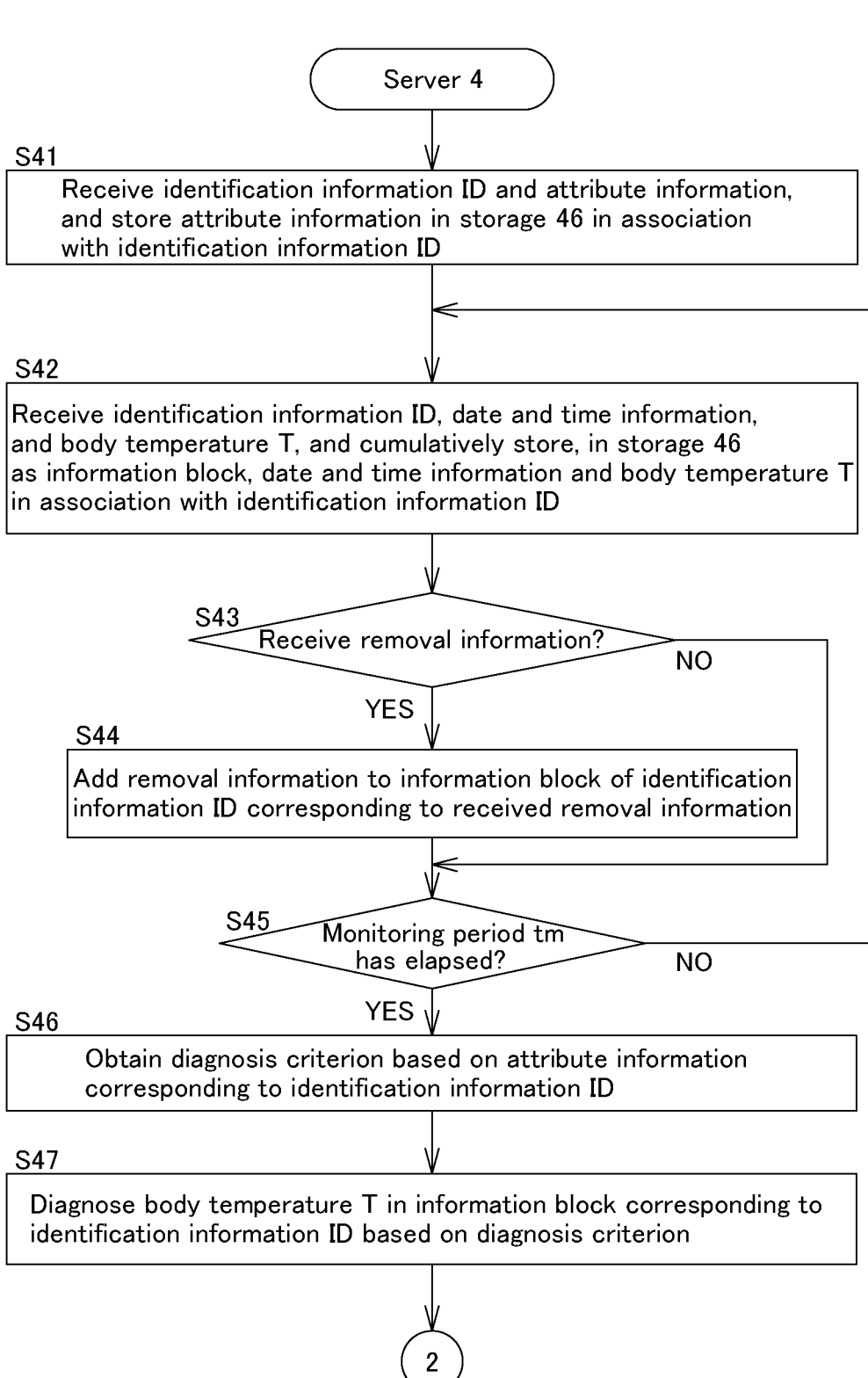
FIG. 9 is a flowchart showing an example of an operation of a server shown in FIG. 1.
Figure 10:
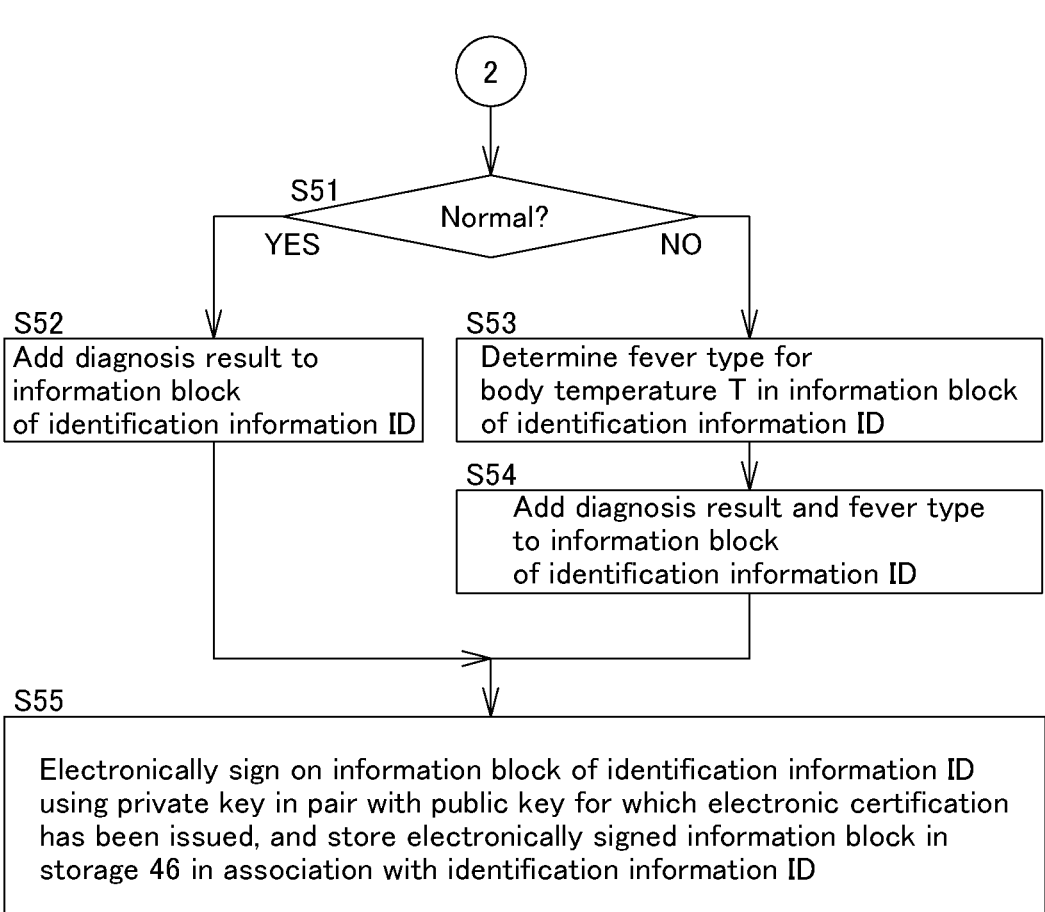
FIG. 10 is a flowchart showing an example of the operation of the server shown in FIG. 1.

FIGS. 9 and 10 are flowcharts each showing an example of an operation of the server 4 shown in FIG. 1. First, the storage processor 41 receives the identification information ID and the attribute information of the information monitoring device 2 via the wireless communication terminal 3, and causes the storage 46 to store the attribute information and the identification information ID in association with each other (Step S41).

Next, the storage processor 41 receives the identification information ID of the information monitoring device 2, date and time information, and a body temperature T via the wireless communication terminal 3, and causes the storage 46 to cumulatively store, as the information block, the date and time information and the body temperature T, in association with the identification information ID (Step S42).

The information management system 1 can include a plurality of information monitoring devices 2, and the server 4 can perform the following processing for the identification information ID of each information monitoring device 2. Here, in the following description, an operation for one information monitoring device 2 will be described for ease of description.

Next, the storage processor 41 checks whether the removal information has been received (Step S43). If the removal information has been received (YES in Step S43), the storage processor 41 adds the removal information to an information block of the identification information ID corresponding to the received removal information (Step S44).

Accordingly, the removal of the information monitoring device 2 corresponding to the identification information ID from the body of a person U during the monitoring period tm is stored in the information block. In other words, it becomes apparent that the body temperatures T of the information block containing the removal information cannot be guaranteed as those of the same person, which have been continuously measured during the monitoring period tm.

On the other hand, if no removal information has been received (NO in Step S43), the storage processor 41 allows processing to proceed to Step S45 without adding removal information to the information block.

In Step S45, the storage processor 41 checks whether the monitoring period tm has elapsed since the body temperature T of the identification information ID was first received (Step S45). If the monitoring period tm has not elapsed (NO in Step S45), processing in Steps S42 to S45 is repeated again.

If the monitoring period tm has elapsed (YES in Step S45), the diagnosis criterion acquirer 44 obtains a diagnosis criterion based on the attribute information corresponding to the identification information ID (Step S46).

Specifically, the diagnosis criterion acquirer 44 can obtain the diagnosis criterion as follows, for example. FIG. 11 is an explanatory diagram showing an example of a diagnosis criterion table stored in the storage 46 in advance. The diagnosis criterion table A shown in FIG. 11 includes nationality, gender, age, height, and a blood type as attributes. A combination of these attributes is associated with a normal body temperature representing the diagnosis criterion, and a variation range of the normal body temperature.

The diagnosis criterion table A can be obtained by, for example, measuring body temperatures T of persons with various attributes for a certain period of time and performing statistic processing on the measurement results.

In step S46, the attribute of a person U includes, for example, nationality=Japan, gender=male, age=20, height=170, blood type=O. The diagnosis criterion acquirer 44 can refers to the diagnosis criterion table A, and obtain a normal body temperature of 36.5° C., and a determination criterion of 36.1-36.9° C. with a variation range of +0.4.

Next, the diagnoser 42 performs diagnosis on the body temperatures T in the information block corresponding to the identification information ID, based on the diagnosis criterion obtained in Step S46 (Step S47). Specifically, if the body temperatures T detected during the monitoring period tm, which are included in the information block corresponding to the identification information ID, are all within the range of 36.1 to 36.9° C., the diagnoser 42 diagnoses as normal (YES in Step S51), and adds a diagnosis result indicating the normality to the information block corresponding to the identification information ID (Step S52).

On the other hand, if even one of the body temperatures T detected during the monitoring period tm, which are contained in the information block corresponding to the identification information ID, is out of the determination criterion of 36.1° to 36.9° C., it is diagnosed as abnormal (NO in Step S51), and a fever type is determined for the body temperatures T in the information block corresponding to the identification information ID (Step S53).

Figure 12:
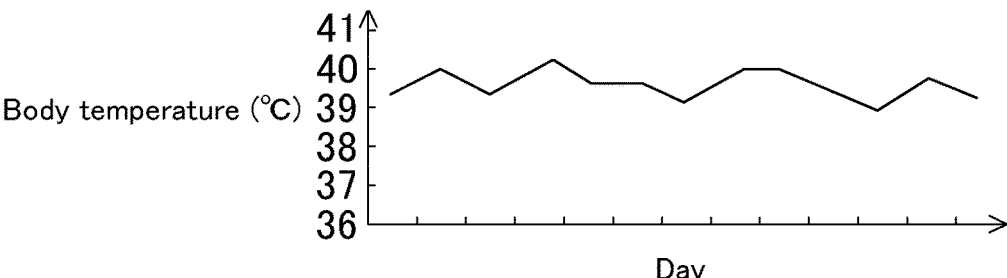
FIG. 12 is a graph showing a fever type known as continuous fever.
Figure 13:
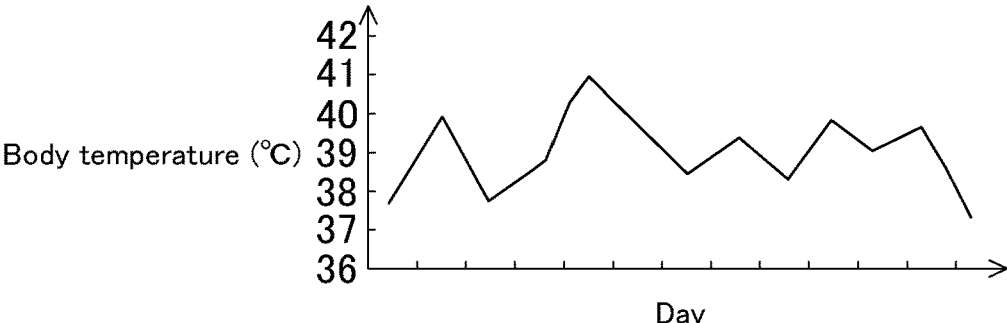
FIG. 13 is a graph showing a fever type known as remittent fever.
Figure 14:
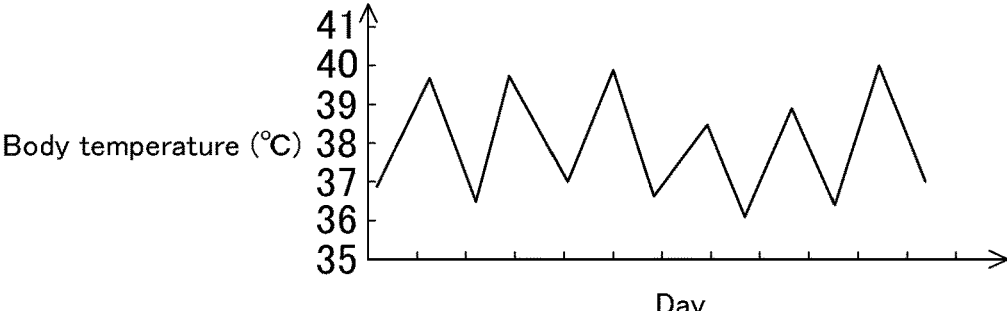
FIG. 14 is a graph showing a fever type known as intermittent fever.
Figure 15:
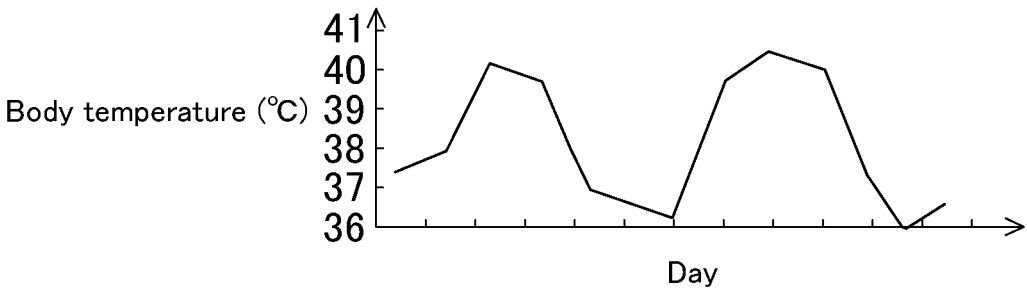
FIG. 15 is a graph showing a fever type known as undulant fever.
Figure 16:
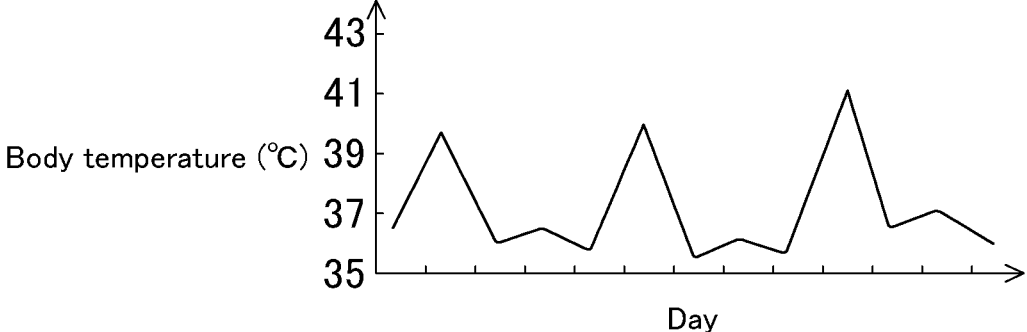
FIG. 16 is a graph showing a fever type known as periodic fever.

FIGS. 12 to 16 are explanatory diagrams each showing an example of the fever type. FIG. 12 is a graph showing a fever type known as continuous fever, in which high fever persists with a temperature difference in a day of less than 1° C. FIG. 13 is a graph showing a fever type known as remittent fever, in which the temperature difference in a day fluctuates by more than 1° C. and fever does not drop below 37° C. FIG. 14 is a graph showing a fever type known as intermittent fever, in which high fever and a normal temperature alternate at regular intervals, and the body temperature fluctuates greatly. FIG. 15 is a graph showing a fever type known as undulant fever, in which a feverish period and an afebrile period are irregularly repeated. FIG. 16 is a graph showing a fever type known as periodic fever, in which fever repeatedly occurs in regular cycles.

In Step S53, the diagnoser 42 determines which one of the continuous fever, remittent fever, intermittent fever, undulant fever, and periodic fever, the body temperatures T in the information block of the identification information ID corresponds to. Then, the diagnoser 42 adds a diagnosis result indicating the abnormality and information indicating the fever type to the information block of the identification information ID (Step S54).

The continuous fever is known to occur in lobar pneumonia, an acme stage of typhoid fever, chestnut tuberculosis, and meningitis. The remittent fever is known to occur in suppurative diseases, sepsis, hypothermia of typhoid fever, viral diseases, malignant tumors, pulmonary tuberculosis, and so on. The intermittent fever is known to occur in malaria and relapsing fever. The undulant fever is known to occur in brucellosis, malaria, Hodgkin's disease, kidney stones, biliary atresia, and so on. The periodic fever is known to be caused by malaria and steroid fever.

As described above, the fever type and the disease are related, and thus the determination of the fever type can be used as a clue for estimating the disease of a person U.

Next, the electronic certification processor 45 provides an electronic signature to the information block of the identification information ID, and stores the information block provided with the electronic signature in the storage 46 in association with the identification information ID (Step S55). Then, the processing is terminated until a request from the terminal 5 is received.

For example, the electronic certification processor 45 obtains, in advance from a certificate authority, an electronic certificate including a public key, and a private key corresponding to the electronic certificate, and causes the storage 46 to store them. The electronic certificate also contains information indicating the certificate authority. This private key can be used to provide electronic signature to the information block of the identification information ID.

Figure 17:
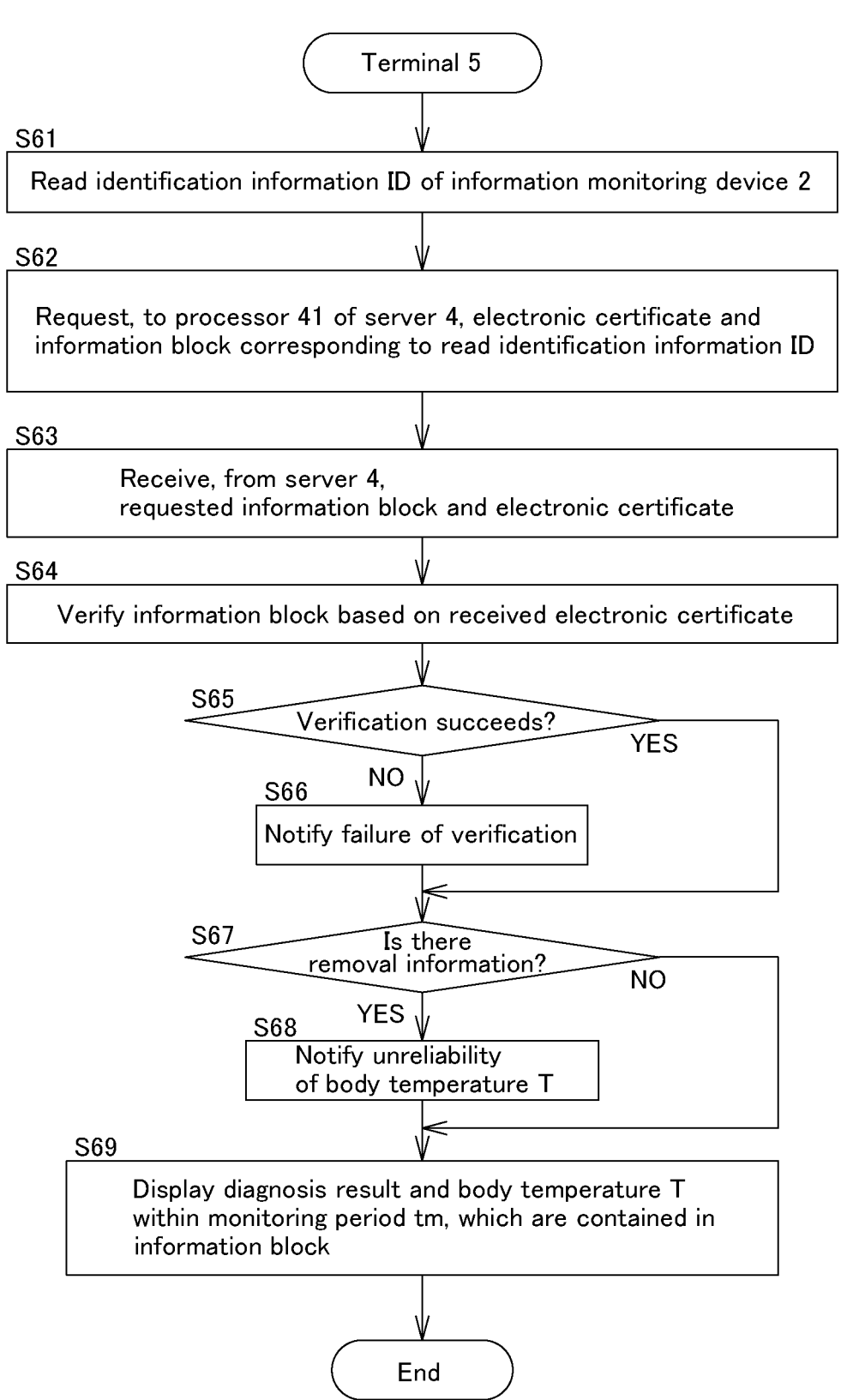
FIG. 17 is a flowchart showing an example of an operation of a terminal shown in FIG. 1.

Next, an operation of the information management system 1 when a person U undergoes an immigration inspection after traveling is described. A case where the terminal 5 is installed, for example, in an immigration office and used by an immigration inspector is described below. FIG. 17 is a flowchart showing an example of an operation of the terminal 5 shown in FIG. 1.

First, when a person U who has traveled arrives at an immigration inspection office to enter the country, an immigration inspector uses a reader 54 to read an image code 213 of the information monitoring device 2 attached to the body of the person U. With this operation, the identification information ID of the information monitoring device 2 attached to the body of the person U is read by the reader 54 (Step S61).

Next, the request processor 51 requests, to the storage processor 41 of the server 4, an information block corresponding to the identification information ID read by the reader 54 and the electronic certificate including the public key (Step S62).

Then, in the server 4, the request from the request processor 51 is received, and the storage processor 41 reads the information block corresponding to the requested identification information ID and the electronic certificate from the storage 46, and transmits them to the terminal 5.

In the terminal 5, the request processor 51 obtains the information block and the electronic certificate, which have been received from the server 4 (Step S63).

Next, the verifier 52 verifies the information block corresponding to the identification information ID based on the received electronic certificate (Step S64).

For example, the verifier 52 may refer to information indicating the certificate authority contained in the electronic certificate; access the certificate authority; and confirm the validity of the electronic certificate. If the electronic certificate is invalid, the verification fails (NO in Step S65). If the electronic certificate is valid, the electronic signature provided to the information block is decrypted to obtain a hash value. Further, the hash value of the information block is referred to. If the hash value matches a hash value obtained from the electronic signature, the verification succeeds (YES in Step S65), and if it does not match, the verification fails (NO in Step S65).

If the verification fails (NO in Step S65), the information notifier 53 displays that the verification has failed on the display 55, for example (Step S66), to perform notification, and allows processing to proceed to Step S67. With this operation, the immigration inspector can deny entry of the person U on the ground that the record of the temperatures T of the person U is unreliable.

On the other hand, if the verification succeeds (YES in Step S65), the processing proceeds to Step S67 without performing processing in Step S66.

In Step S67, the information notifier 53 checks whether the removal information is contained in the information block of the identification information ID received from the server 4 (Step S67). If the removal information is contained (YES in Step S67), the information notifier 53 notifies that the removal information is contained in the information block, or that the record of the body temperatures T of the person U is unreliable, by displaying such information on the display 55, for example (Step S68), and allows the processing to proceed to Step S69.

Here, if the removal information is not contained (NO in Step S67), the information notifier 53 allows processing to proceed to Step S69 without performing processing in Step S68.

If the removal information is contained in the information block (YES in Step S67), there is a possibility that the information monitoring device 2 was removed from the person U during the monitoring period tm. As a result, there may be a period, during the monitoring period tm, in which the body temperature T contained in the information block was not detected and was missed, or the information monitoring device 2 might be attached to another person different from the person U and the body temperature might be of another person. Therefore, if it is notified in Step S68 that the removal information is contained in the information block, or that the record of the body temperatures T of the person U is unreliable, the immigration inspector can deny entry of the person U on the grounds that the record of the body temperatures T of the person U is unreliable.

It should be noted that the information notifier 53 is not limited to displaying information such as verification failure and removal information on the display 55 in Steps S66 and S68. The information notifier 53 may perform the notification by emitting an alarm sound, for example.

In Step S69, the information notifier 53 causes the display 55 to display the diagnosis result and the body temperatures T measured within the monitoring period tm, which are included in the information block of the identification information ID (Step S69). With this operation, the immigration inspector can deny entry of the person U when the diagnosis result indicates an abnormality. In addition, the immigration inspector can also deny entry of the person U if the immigration inspector determines that the person U is suspected of having an infectious disease or the like by checking the temperatures T of the person U during the monitoring period tm. Alternatively, the terminal 5 or the server 4 may determine whether the person U can enter the country.

For example, for the purpose of preventing infection of an infectious disease caused by viruses, it is conceivable to restrict the entry of the person U from a country A where the infectious disease is spreading, to a country B. In this case, in the country A, for example, the person U may attach the information monitoring device 2 to his/her body for the monitoring period tm (for example, 14 days) before departure, may travel to the country B when the monitoring period tm has passed, and then can undergo the immigration inspection or quarantine.

In this case, an immigration inspector or a quarantine officer uses the terminal 5, when the person U enters country B, to confirm that the body temperatures T during the monitoring period tm before entering country B are continuously detected, thereby effectively imposing immigration restrictions to prevent infection.

Furthermore, if a polymerase chain reaction (PCR) test is performed on a person U before leaving country A, for example, and the result of the PCR test and the body temperatures T during the monitoring period tm obtained by the information monitoring device 2 are used, the certainty of confirming a status of the infection is improved. As a result, it becomes easy to shorten a waiting period after the person U enters the country B, or to make the waiting unnecessary.

Next, a method of managing admission to an event venue or the like using the information management system 1 is described. If the information management system 1 is used to manage admission to an event venue, etc., it is preferable to sell the information monitoring device 2 as a ticket.

For example, it is preferable that the information monitoring device 2 is to be sold with information necessary for a ticket, such as "ticket for XX concert, date: month X, day X, year X" being printed on the surface of a sheet member of the information monitoring device 2 in a manner of preventing the image code 213 from being overlapped. Then, a person U who purchased the ticket attaches the information monitoring device 2 to his/her body for a monitoring period tm (for example, 14 days) before the event or the like is held. On the day of the event, a person in charge of admission management reads the image code 213 using the reader 54 of the terminal 5 at the entrance of the event venue. Furthermore, the admission manager may use the terminal 5 to obtain the body temperatures T of the person U during the monitoring period tm, the diagnosis result, the removal information, and so on, from the server 4, and may determine whether the person U is allowed to enter, based on the information, the verification result, and so on. Alternatively, the admission of the person U can be determined by the terminal 5 or the server 4.

As described above, if the information management system 1 is used to manage admission to an event or the like, entry of a person U who is suspected of having an infectious disease or the like is avoided based on the body temperatures T of the person U during the monitoring period tm. Therefore, admission management for preventing infection can be effectively performed.

If the information management system 1 is used for the admission management, it is not necessary for the information monitoring device 2 itself to be a ticket. Aside from the ticket, the information monitoring device 2 may be attached to the body of a person U who purchased the ticket.

The target information is not limited to the body temperature T. The target information may be, for example, vital signs such as heartbeat, pulse, blood pressure, pulse pressure, electrocardiogram, blood oxygen concentration, and respiratory rate. Furthermore, the measurement target is not limited to humans, and the target information is not limited to such vital signs.

For example, it is assumed that the measurement target may be vintage wine and the target information is a temperature. The information monitoring device 2 is attached to a bottle of the vintage wine to monitor the temperature of the wine. When the wine is sold, a purchaser can check the temperature history recorded in the server 4 using the terminal 5. Thus, it is possible to show the purchaser that the expensive vintage wine has been properly temperature-controlled, and thus an additional value of quality control can be provided.

In addition, the removal detector is not limited to the optical sensor 215, as long as it can detect the removal of the temperature sensor 214 from the measurement target. As the removal detector, a contact sensor, for example, may be used instead of the optical sensor 215.

In addition, the temperature sensor 214 may be used as the removal detector instead of the optical sensor 215. Then, after the body temperature T detected by the temperature sensor 214 exceeds a temperature considered to be a human body temperature, e.g., 35° C., the body temperature T may fall below a temperature that is not normally considered as a human body temperature, e.g., 33° C. At this time, the removal determiner 14 may determine that the information monitoring device 2 has been removed, and transmit the removal information to the wireless communication terminal 3 in Step S16.

Alternatively, a sensor that detects target information different from the temperatures may be used as the removal detector, instead of the optical sensor 215, and may detect the removal of the sensor from the measurement target based on such target information.

Further, the removal detector may be a member that detects removal of the information monitoring device 2 including a sensor from a measurement target by developing a predetermined pattern or changing its color when at least a part of the sheet member constituting the holding member 22 is peeled off after being attached to the measurement target. For such a member, members respectively disclosed in JP 61-226783 A, JP 2014-044451 A, JP 7-234636 A, JP 2004-212778 A, and JP 2005-148325 A, can be used, for example. When such members are used, there is no necessity to provide the removal determiner 14, and processing in Steps S15, S16, S43, S44, S67, and S68 is unnecessary.

Moreover, the holding member is not limited to the sheet member. The holding member may be, for example, an adhesive (glue) that directly affixes the circuit 21 to the measurement target. Furthermore, the holding member may be, for example, a belt or the like, and may not have the adhesive layer 223.

Alternatively, the activation controller 11 may not be provided, and the processing may be shifted from Step S5 to Step S7 without performing processing in Step S6.

Further, the specific phenomenon is not limited to a body temperature T that exceeds the specific body temperature Ts. The specific phenomenon may be appropriately set according to a type and characteristic of the information that is to be the target information, and a monitoring purpose of the information monitoring device.

Also, the information monitoring device 2 may not include the power controller 216. For example, the information monitoring device 2 may include a power switch for turning on/off power supply from the battery 212, or power may be constantly supplied from the battery 212 to each part in the circuit 21.

Further, applications of the information monitoring device 2 and the information management system 1 are not limited to the immigration control or the admission control, but can be used for various purposes.

The server 4 or the terminal 5 may include the attribute receptor 302. The information management system 1 may not include the wireless communication terminal 3, and the information monitoring device 2 may communicate with the server 4 or the terminal 5 without the wireless communication terminal 3 that intervenes between them.

Further, the storage processor 41, the diagnoser 42, the attribute acquirer 43, the diagnosis criterion acquirer 44, the electronic certification processor 45, and the storage 46 are not limited to be included in the server 4. At least one of the storage processor 41, the diagnoser 42, the attribute acquirer 43, the diagnosis criterion acquirer 44, the electronic certification processor 45, and the storage 46 may be included in any one of the information monitoring device 2, the wireless communication terminal 3, and the terminal 5, or may be distributed to and included in the information monitoring device 2, the wireless communication terminal 3, and the terminal 5.

Also, the information management system 1 may not include the server 4. The information management system 1 may not include the information monitoring device 2.

Further, the information management system 1 may not include the electronic certification processor 45 and the verifier 52, and may not perform processing in Steps S55 and S64 to S66.

Further, the information management system 1 may not include the attribute acquirer 43 and the diagnosis criterion acquirer 44, and may not perform processing in Steps S41 and S46. The diagnosis criterion may be fixed in advance.

Further, the diagnoser 42 may not determine the fever type, and may not perform processing in Step S53. The information management system 1 may not include the diagnoser 42 and may not perform processing in Steps S41, S46, S47, and S51 to S54.

In other words, an information monitoring apparatus according to one aspect of the present invention is an information monitoring apparatus for monitoring information, which includes a sensor that detects predetermined target information from a measurement target; a detection controller that performs control on the sensor so that the sensor repeatedly detects the target information; a holding member that attaches the sensor to the measurement target to hold the sensor; and a removal detector that detects removal of the sensor from the measurement target.

According to the configuration, it is possible to repeatedly detect the target information from the measurement target. Furthermore, when the sensor is removed from the measurement target, the removal can be detected, thereby making it easy to confirm that the detected information is continuously detected information.

It is preferable that the removal detector includes an optical sensor that is shielded from light in a surrounding environment when the sensor is attached to the measurement target, and receives the light in the surrounding environment when the sensor is removed from the measurement target.

According to the configuration, when the sensor is removed from the measurement target, light from the surrounding environment is received by the optical sensor, whereby the light from the surrounding environment is detected by the optical sensor. Accordingly, the removal of the sensor from the measurement target can be detected.

It is preferable to further include a releasable sheet attached to an attachment surface of the information monitoring device in a peelable manner, the attachment surface being intended to be attached to the measurement target, in which the releasable sheet shields the optical sensor from the surrounding environment while being attached to the attachment surface; and the removal detector further includes a removal determiner that determines the removal of the sensor from the measurement target, at second detection of predetermined light by the optical sensor, after first detection of the predetermined light by the optical sensor and following no detection of the predetermined light by the optical sensor.

According to this configuration, before the information monitoring device is attached to the measurement target, the releasable sheet is attached to the attachment surface to shield the optical sensor from light in a surrounding environment. When the releasable sheet is peeled off to attach the information monitoring device to the measurement target, the light of the surrounding environment is detected by the optical sensor. Thereafter, the information monitoring device is attached to the measurement target, causing the optical sensor to be shielded from the light in the surrounding environment, and thus causing the optical sensor to no longer detect the light. Further, if the sensor is then removed from the measurement target, the light in the surrounding environment is detected by the optical sensor, thereby detecting light by the optical sensor. Therefore, the removal determiner determines that the sensor is removed from the measurement target, at the second detection of the predetermined light by the optical sensor after the first detection of the predetermined light by the optical sensor and the following no detection of the predetermined light by the optical sensor.

It is preferable to further include a releasable sheet attached to an attachment surface of the information monitoring device in a peelable manner, the attachment surface being intended to be attached to the measurement target; a battery that supplies power for allowing the information monitoring device to operate; and a power controller that causes the battery to start supplying the power when predetermined light is detected by the optical sensor, in which the releasable sheet shields the optical sensor from the surrounding environment while being attached to the attachment surface.

According to this configuration, when the user peels off the releasable sheet to start using the information monitoring device, light in a surrounding environment is detected by the optical sensor, and power supply from the battery is started. Accordingly, the power supply from the battery can be cut off until the releasable sheet is peeled off from the information monitoring device, thereby reducing a risk of the battery running out while the information monitoring device is kept without being used.

It is preferable to further include an activation controller that causes the detection controller to perform the control, when the predetermined light is not detected by the optical sensor after the predetermined light is detected by the optical sensor.

According to the configuration, the information monitoring device is attached to the measurement target and the target information can be detected by the sensor, after the releasable sheet is peeled off and the optical sensor detects the predetermined light. Then, the target information is obtained. This can reduce the possibility that the environmental temperature or the like before the information monitoring device is attached to the measurement target is erroneously detected as the target information.

It is preferable that the removal detector detects the removal of the sensor from the measurement target based on the target information detected by the sensor.

According to this configuration, when the sensor is removed from the measurement target, the sensor cannot detect the target information from the measurement target. Therefore, the removal detector can detect that the sensor has been removed from the measurement target based on the target information detected by the sensor.

It is preferable that the holding member is a sheet member provided with an adhesive layer that adheres to the measurement target.

According to the configuration, the information monitoring device can be affixed to the measurement target by the adhesive layer.

Further, the removal detector may include a member that is provided in at least a part of the sheet member and detects the removal of the sensor from the measurement target by developing a predetermined pattern or changing a color of the member, when the member is peeled off from the measurement target after being attached to the measurement target.

According to the configuration, when the information monitoring device is attached to the measurement target and then peeled off therefrom, at least a part of the sheet member develops a predetermined pattern or changes its color. As a result, the removal of the sensor from the measurement target can be visually recognized, and the removal of the sensor from the measurement target can be detected.

It is preferable that the sheet member is a ticket.

According to the configuration, the information monitoring device can be used as a ticket.

It is preferable that the detection controller shortens an interval of detection by the sensor, when the target information corresponds to a specific phenomenon set in advance.

If the detection interval is shortened, the target information is detected more frequently. While the frequency of detecting the target information can be reduced to reduce power consumption, processing load, and the like, the frequency of detecting the target information can be increased at the time when the necessity of increase in the frequency of detecting target information is high. Accordingly, the monitoring accuracy of the target information can be improved.

An information management system according to an aspect of the present invention includes the information monitoring device described above; a storage that stores information; and a storage processor that causes the storage to cumulatively store the target information repeatedly detected.

According to this configuration, the target information repeatedly detected is cumulatively stored in the storage by the information management system including the above-described information monitoring device.

An information management system according to an aspect of the present invention includes a storage that stores information obtained from the information monitoring device described above; and a storage processor that causes the storage to cumulatively store the target information repeatedly detected.

According to this configuration, the information monitoring device described above may be out of the information management system, and the target information repeatedly detected by the information monitoring device described above is cumulatively stored in the storage.

It is preferable to further include a diagnoser that performs diagnosis based on a plurality of pieces of target information.

According to this configuration, diagnosis can be performed based on a plurality of pieces of the target information.

It is preferable that the measurement target is a human; the target information is a body temperature; and the diagnoser determines a fever type from a plurality of body temperatures including the body temperature.

According to this configuration, it is possible to determine the fever type of a person by monitoring body temperatures of the person.

It is preferable to further include an attribute acquirer that obtains attribute information indicating an attribute of the measurement target; and a diagnosis criterion acquirer that obtains a diagnosis criterion serving as a criterion for the diagnosis, based on the attribute information, in which the diagnoser performs the diagnosis based on the diagnosis criterion.

According to this configuration, diagnosis can be performed using the diagnosis criterion corresponding to an attribute of the measurement target, thereby improving the accuracy of the diagnosis.

It is preferable that the measurement target is a human; the target information is a vital sign; and the attribute is at least one of nationality, gender, age, height, weight and a blood type.

According to this configuration, the condition of a person can be diagnosed using the diagnosis criterion according to the attribute of the person, thereby improving the accuracy of diagnosis.

It is preferable that the information monitoring device is provided with identification information for identifying the information monitoring device itself; the storage processor causes the storage to store an information block containing a plurality of pieces of target information, in association with the identification information, the plurality of pieces of target information including the target information; the information management system further includes a terminal capable of requesting processing to the storage processor; and the terminal includes a reader that reads the identification information from the information monitoring device; and a request processor that requests and obtains, to/from the storage processor, the information block associated with the identification information read by the reader.

According to this configuration, the terminal is used to read the identification information from the information monitoring device, and the information block associated with the identification information is requested to the storage processor and thus obtained. In other words, the target information detected by the information monitoring device and cumulatively stored can be confirmed by the terminal.

It is preferable that the information monitoring device is provided with identification information for identifying the information monitoring device itself; the storage processor causes the storage to store the identification information in association with the information block containing at least one of a diagnosis result of the diagnoser and the plurality of pieces of target information; the information management system further includes a terminal capable of requesting processing to the storage processor; and the terminal includes a reader that reads the identification information from the information monitoring device; and a request processor that requests and obtains, to/from the storage processor, the information block associated with the identification information read by the reader.

According to this configuration, the terminal is used to read the identification information from the information monitoring device, and the information block associated with the identification information can be obtained by being requested to the storage processor. In other words, at least one of the target information and the diagnosis result, which are detected by the information monitoring device and cumulatively stored, can be checked by the terminal.

It is preferable to further include an electronic certification processor that provides an electronic signature to the information block using a private key in pair with an electronic certification containing a public key, and causes the storage to store the information block provided with the electronic signature in association with the identification information, in which the request processor that requests and obtains, to/from the storage processor, the electronic certification and the information block that is provided with the electronic signature and associated with the identification information read by the reader, and the terminal further includes a verifier that verifies the information block provided with the electronic signature by using the electronic certification obtained by the request processor.

According to the configuration, it is possible to prevent tampering with the information block containing the cumulatively stored target information. Therefore, the certainty of the detected target information being continuously-detected information is enhanced.

An immigration inspection method according to an aspect of the present invention uses the information management system described above, in which when a person who wears the information monitoring device enters a country, an immigration inspection or quarantine is performed based on the information block obtained by the terminal.

The configuration improves the certainty that the target information detected from a person who wears the information monitoring device is the information continuously detected. As a result, the certainty in the immigration inspection or quarantine is improved.

An admission management method according to an aspect of the present invention uses the information management system described above. The method includes selling the information monitoring device as a ticket; and determining, at admission of a person wearing the information monitoring device, whether the admission is allowed, based on the information block obtained by the terminal.

The configuration improves the certainty that the target information detected from a person who wears the information monitoring device is the information continuously detected. As a result, the certainty in determining the propriety of the admission is improved.

A computer-readable recording medium storing an information management program according to an aspect of the present invention causes a computer to function as a storage that stores information obtained from the information monitoring device described above; and a storage processor that causes the storage to cumulatively store the target information repeatedly detected.

The information management program can cause the computer to function as a storage, a storage processor, and the like.

With the information monitoring device, information management system, immigration inspection method, admission management method, and information management program configured as above, it becomes easy to confirm that the detected information is continuously detected information.

This application is based on Japanese Patent Application No. 2020-110146 filed on Jun. 26, 2020, the content of which is incorporated herein. It should be noted that the specific embodiments or examples described in paragraphs for carrying out the invention merely clarify the technical content of the present invention, and the present invention should not be interpreted narrowly by being limited to such specific examples.

What is claimed is:

1. An information monitoring device for monitoring information, comprising:

a sensor that detects predetermined target information from a measurement target;

a detection controller that performs control on the sensor so that the sensor repeatedly detects the target information;

a holding member that attaches the sensor to the measurement target to hold the sensor; and a removal detector that detects removal of the sensor from the measurement target upon detection of light in a surrounding environment, wherein the removal detector includes an optical sensor that is shielded from light in a surrounding environment when the sensor is attached to the measurement target, and receives the light in the surrounding environment when the sensor is removed from the measurement target, and wherein the removal detector further determines the removal of the sensor from the measurement target, at second detection of predetermined light by the optical sensor, after first detection of the predetermined light by the optical sensor and following no detection of the predetermined light by the optical sensor.

2. The information monitoring device according to claim 1, further comprising: a releasable sheet attached to an attachment surface of the information monitoring device in a peelable manner, the attachment surface being intended to be attached to the measurement target, wherein the releasable sheet shields the optical sensor from the surrounding environment while being attached to the attachment surface.

3. The information monitoring device according to claim 1, comprising: a releasable sheet attached to an attachment surface of the information monitoring device in a peelable manner, the attachment surface being intended to be attached to the measurement target; a battery that supplies power for allowing the information monitoring device to operate; and a power controller that causes the battery to start supplying the power when predetermined light is detected by the optical sensor, wherein the releasable sheet shields the optical sensor from the surrounding environment while being attached to the attachment surface.

4. The information monitoring device according to claim 2 or 3, further comprising:

an activation controller that causes the detection controller to perform the control, when the predetermined light is not detected by the optical sensor after the predetermined light is detected by the optical sensor.

5. The information monitoring device according to claim 1, wherein the removal detector detects the removal of the sensor from the measurement target based on the target information detected by the sensor.

6. The information monitoring device according to claim 1, wherein the holding member is a sheet member provided with an adhesive layer that adheres to the measurement target.

7. The information monitoring device according to claim 6, wherein the removal detector includes a member that is provided in at least a part of the sheet member and detects the removal of the sensor from the measurement target by developing a predetermined pattern or changing a color of the member, when the member is peeled off from the measurement target after being attached to the measurement target.

8. The information monitoring device according to claim 6, wherein the sheet member is a ticket.

9. The information monitoring device according to claim 1, wherein the detection controller shortens an interval of detection by the sensor, when the target information corresponds to a specific phenomenon set in advance.

10. An information management system comprising:

the information monitoring device according to claim 1;

a storage that stores information; and a storage processor that causes the storage to cumulatively store the target information repeatedly detected.

11. An information management system comprising:

a storage that stores information obtained from the information monitoring device according to claim 1; and a storage processor that causes the storage to cumulatively store the target information repeatedly detected.

12. The information management system according to claim 11, further comprising:

a diagnoser that performs diagnosis based on a plurality of pieces of target information.

13. The information management system according to claim 12, wherein the measurement target is a human;

the target information is a body temperature; and the diagnoser determines a fever type from a plurality of body temperatures including the body temperature.

14. The information management system according to claim 12, further comprising:

an attribute acquirer that obtains attribute information indicating an attribute of the measurement target; and a diagnosis criterion acquirer that obtains a diagnosis criterion serving as a criterion for the diagnosis, based on the attribute information, wherein the diagnoser performs the diagnosis based on the diagnosis criterion.

15. The information management system according to claim 14, wherein the measurement target is a human;

the target information is a vital sign; and the attribute is at least one of nationality, gender, age, height, weight and a blood type.

16. The information management system according to claim 10, wherein the information monitoring device is provided with identification information for identifying the information monitoring device itself;

the storage processor causes the storage to store an information block containing a plurality of pieces of target information, in association with the identification information, the plurality of pieces of target information including the target information;

the information management system further comprises a terminal capable of requesting processing to the storage processor; and the terminal includes:

a reader that reads the identification information from the information monitoring device; and a request processor that requests and obtains, to/from the storage processor, the information block associated with the identification information read by the reader.

17. The information management system according to claim 12, wherein the information monitoring device is provided with identification information for identifying the information monitoring device itself;

the storage processor causes the storage to store the identification information in association with the information block containing at least one of a diagnosis result of the diagnoser and the plurality of pieces of target information;

the information management system further comprises a terminal capable of requesting processing to the storage processor; and the terminal includes:

a reader that reads the identification information from the information monitoring device; and a request processor that requests and obtains, to/from the storage processor, the information block associated with the identification information read by the reader.

18. The information management system according to claim 16 or 17, further comprising:

an electronic certification processor that provides an electronic signature to the information block using a private key in pair with an electronic certification containing a public key, and causes the storage to store the information block provided with the electronic signature in association with the identification information, wherein the request processor that requests and obtains, to/from the storage processor, the electronic certification and the information block that is provided with the electronic signature and associated with the identification information read by the reader, and the terminal further includes a verifier that verifies the information block provided with the electronic signature by using the electronic certification obtained by the request processor.

19. An immigration inspection method that uses the information management system according to claim 16, wherein when a person who wears the information monitoring device enters a country, an immigration inspection or quarantine is performed based on the information block obtained by the terminal.

20. An admission management method that uses the information management system according to claim 16, the method comprising:

selling the information monitoring device as a ticket; and determining, at admission of a person wearing the information monitoring device, whether the admission is allowed, based on the information block obtained by the terminal.

21. A computer-readable recording medium storing an information management program that causes a computer to function as:

a storage that stores information obtained from the information monitoring device according to claim 1; and a storage processor that causes the storage to cumulatively store the target information repeatedly detected.

* * * * *